(12) United States Patent
Sabater et al.

(10) Patent No.: US 11,154,052 B2
(45) Date of Patent: Oct. 26, 2021

(54) DUAL-CHAMBER VIAL FOR CORNEAL GRAFT PRESERVATION

(71) Applicants: University of Miami, Coral Gables, FL (US); TissueCor, LLC, Miami, FL (US)

(72) Inventors: Alfonso L. Sabater, Miami, FL (US); Alejandro M. Sabater, Miami, FL (US); William B. Buras, Miami, FL (US)

(73) Assignees: University of Miami, Coral Gables, FL (US); TissueCor, LLC, Miami, FL (US)

( * ) Notice: Subject to any disclaimer, the term of this patent is extended or adjusted under 35 U.S.C. 154(b) by 0 days.

(21) Appl. No.: 17/275,900

(22) PCT Filed: Sep. 14, 2019

(86) PCT No.: PCT/US2019/051200
§ 371 (c)(1),
(2) Date: Mar. 12, 2021

(87) PCT Pub. No.: WO2020/056392
PCT Pub. Date: Mar. 19, 2020

(65) Prior Publication Data
US 2021/0244020 A1 Aug. 12, 2021

Related U.S. Application Data

(60) Provisional application No. 62/731,338, filed on Sep. 14, 2018.

(51) Int. Cl.
*A01N 1/02* (2006.01)
*A61F 2/00* (2006.01)

(52) U.S. Cl.
CPC .......... *A01N 1/0273* (2013.01); *A61F 2/0095* (2013.01)

(58) Field of Classification Search
None
See application file for complete search history.

(56) References Cited

U.S. PATENT DOCUMENTS 4,205,747 A * 6/1980 Gilliam ................ A45C 11/005
206/5.1
4,844,242 A  7/1989 Chen et al.
(Continued)

FOREIGN PATENT DOCUMENTS

AU  7916891 A  1/1993
CN  102036555 A  4/2011
(Continued)

OTHER PUBLICATIONS

International Search Report and Written Opinion for PCT Application No. PCT/US2019/051200, dated Dec. 4, 2019, International Searching Authority: US, 9 pages.

*Primary Examiner* — William H. Beisner
(74) *Attorney, Agent, or Firm* — Katherine Koenig; Koenig IP Works, PLLC

(57) ABSTRACT

A device and method for preserving corneal graft tissue. In one embodiment, a device for preserving corneal graft tissue comprises: a first chamber; a second chamber; and a corneal graft tissue suspension assembly that is configured to retain and suspend the corneal graft tissue between the first chamber and the second chamber, the first chamber being fluidly isolated from the second chamber when the corneal graft tissue is graft tissue is retained and suspended within the corneal graft tissue suspension assembly. In one embodiment, a method includes filling a first chamber of a device with a first preservation medium and filling a second chamber of the device with a second preservation medium different than or the same as the first, a corneal graft tissue being located between the first and second chambers.

9 Claims, 11 Drawing Sheets

(56) References Cited

U.S. PATENT DOCUMENTS

| | | | |
|---|---|---|---|
| 4,873,193 A | | 10/1989 | Jensen et al. |
| 5,032,131 A | * | 7/1991 | Aysta .................... A61F 2/0095 |
| | | | 623/66.1 |
| 5,104,787 A | | 4/1992 | Lindstrom et al. |
| 5,166,048 A | | 11/1992 | Soll et al. |
| 5,928,935 A | | 7/1999 | Reuss, Jr. et al. |
| 7,371,513 B2 | | 5/2008 | Steinhardt |
| 7,601,487 B2 | | 10/2009 | Soll et al. |
| 10,188,097 B2 | | 1/2019 | Gain et al. |
| 2005/0149055 A1 | | 7/2005 | Briday et al. |
| 2007/0275365 A1 | | 11/2007 | Lui |
| 2016/0029618 A1 | | 2/2016 | Gain et al. |

FOREIGN PATENT DOCUMENTS

| | | | |
|---|---|---|---|
| CN | 206583758 U | * | 10/2017 |
| CN | 109221093 A | | 1/2019 |
| EP | 0891133 B1 | | 11/2004 |
| EP | 1634497 A1 | | 3/2006 |
| EP | 1516532 B1 | | 10/2007 |
| KR | 101304014 B1 | | 9/2013 |
| RU | 2184448 C2 | | 7/2002 |
| RU | 2676311 C1 | | 12/2018 |
| WO | 2008131973 A2 | | 11/2008 |
| WO | 2010099414 A2 | | 9/2010 |
| WO | 2020/056392 A1 | | 3/2020 |

* cited by examiner

DUAL-CHAMBER VIAL FOR CORNEAL GRAFT PRESERVATION

CROSS-REFERENCE TO RELATED APPLICATIONS

This application is a Submission under 35 U.S.C. § 371 for U.S. National Phase Patent Application of, and claims priority to, International Application Number PCT/US2019/051200, entitled DUAL-CHAMBER VIAL FOR CORNEAL GRAFT PRESERVATION, filed Sep. 14, 2019, which is related to and claims priority to U.S. Provisional Patent Application Serial No. 62/731,338, filed Sep. 14, 2018, entitled DUAL-CHAMBER VIAL FOR CORNEAL GRAFT PRESERVATION, now expired, the entirety of all of which is incorporated herein by reference.

TECHNICAL FIELD

This disclosure relates to a device and method for storing and preserving corneal graft tissue.

INTRODUCTION

Corneal transplants or grafts are the most common and successful transplantation procedures in medicine. In fact, more than 280,000 donor corneas are recovered every year and at least 180,000 corneal transplants are performed worldwide. According to a global survey that was conducted between 2012 and 2013, around 40% of the corneas were recovered in the United States (Gain, P., et al., "Global Survey of Corneal Transplantation and Eye Banking," *JAMA Ophthalmology*, 2016, 134(2), 167-173). The terms "corneal transplant" and "corneal graft" are used interchangeably herein, and the term "corneal graft tissue" is used herein to refer to the tissue grafted or transplanted used for the corneal transplant or graft procedure.

The cornea is the clear, protective outer layer of the eye, and consists primarily of three layers, namely, the epithelium (outer layer), the stroma, and the endothelium (inner layer). Each layer has different characteristics. The corneal epithelium is a thin multicellular epithelial tissue layer of fast-growing and easily regenerated cells.

The corneal stroma is a thick, transparent middle layer that includes regularly arranged collagen fibers and keratocytes, which are the cells that help to maintain the structure of the stroma. The corneal stroma consists of approximately 200 layers of mainly type I and type V collagen fibers. Up to 90% of the corneal thickness is composed of stroma.

Finally, the corneal endothelium is a monolayer of mitochondria-rich cells. These cells are responsible for regulating fluid and solute transport between the aqueous humor and corneal stroma. Unlike the corneal epithelium, endothelial cells do not regenerate. Instead, they stretch to compensate for dead cells, which reduces the overall cell density of the endothelium and, in turn, affects fluid regulation. If endothelial cells can no longer maintain a proper fluid balance, stromal swelling due to excess fluids and subsequent loss of transparency will occur, which may cause corneal edema and interference with the transparency of the cornea.

The successful outcome of the majority of corneal transplants depends on the presence of a viable corneal endothelium in the corneal graft tissue. In fact, according to Nishimura et al., corneal grafts with late endothelial failure, which is the major cause of graft failure after 5 postoperative years, fail from low initial endothelial cell density rather than an increased rate of chronic postoperative cell loss (Nishimura, J. K., et al., "Initial endothelial cell density and chronic endothelial cell loss rate in corneal transplants with late endothelial failure," *Ophthalmology*, 1999, 106(10), 1962-1965).

Since human corneal endothelial cells do not proliferate in vivo, preservation of the endothelium is a primary goal of methods of corneal storage.

Cryopreservation allows for the preservation of viable tissue for long term. However, despite some successful cryopreserved corneal grafts, its potential for causing endothelial damage have limited its application (Armitage, W. J., "Cryopreservation for corneal storage," *Dev. Ophthalmol.*, 2009, 43, 63-69). On the other hand, hypothermic storage is the most widely applied method in the United States and world-wide (Frueh, B. E., et al., "Prospective, randomized clinical evaluation of Optisol vs organ culture corneal storage media," *Arch. Ophthalmol.*, 2000, 118(6), 757-760). Using specific corneal storage media, corneas can be preserved up to 14 days at 2-8° C. (Frueh, et al., 2000, supra). In contrast, long term preservation at 28-37° C. (organ culture) is the preferred method of storage in Europe, and allows storage time to be extended up to four weeks. However, this medium causes the cornea to swell significantly and requires that this swelling be reversed prior to transplantation by storing it in a secondary medium contain an osmotic agent. Although organ culture preservation offers longer storage time, the more complex logistics as well as the concerns regarding the use of fetal calf serum has restricted its application in several countries, including the United States (Pels, E., et al., "Organ culture preservation for corneal tissue, Technical and quality aspects," *Dev. Ophthalmol.* Basel: KARGER, 2009, 43, 31-46).

Ideally, corneal graft preservation media should be able to maintain a high endothelial cell viability but also prevent corneal swelling during prolonged storage. To prevent corneal swelling, hypothermic preservation media contain colloidal osmotic agents, such as dextran, hydroxyethyl starch or albumin, among others. In particular, dextran is the most commonly used agent in the United States. However, dextran has been shown to have a toxic effect on corneal endothelial cells when they are incubated at 37° C. As shown by Filev et al., the mean endothelium cell loss of organ-cultured corneal explants in dextran-containing media was 2.063% per day, which was 2.9 fold higher than the mean endothelial cell reduction in dextran-free media (0.695% per day) (Filev, F., et al., "Semi-quantitative assessments of dextran toxicity on corneal endothelium: conceptual design of a predictive algorithm," *Cell Tissue Bank*, 2017, 18(1), 91-98). In addition, research has shown that corneal endothelial cells preserved in vitro in hypothermic conditions for up to 48 hours, followed by a transition to standard culture conditions (37° C., 5% $CO_2$), had a significantly lower viability when the hypothermic preservation medium contained dextran, even when the culture medium was dextran-free (Corwin, W. L., et al., "The unfolded protein response in human corneal endothelial cells following hypothermic storage: implications of a novel stress pathway," *Cryobiology*, 2011, 61(1), 46-55). Therefore, although dextran toxicity has not been reported when corneas are preserved at 2-8° C., it seems that endothelial damaged may be induced when corneas are rewarmed either at the eye bank, in the operating room, or even after corneal transplantation. As dextran is absorbed by the corneal endothelium (Redbrake, C., et al., "A histochemical study of the distribution of dextran 500 in human corneas during organ culture," *Curr. Eye Res.*, 1997, 16(5), 405-411), it could have a retarded toxic effect that may contribute to the rapid rate of endothelial cell loss following any corneal transplant procedure. Additionally, it was recently reported that donor grafts usually contain dead cells that remain attached to the cornea, and cannot be identified by specular microscopy (Kitazawa, K., et al., "The existence of dead cells in donor corneal endothelium preserved with storage media," *British J. Ophthalmology*, 2017, 101(12), 1725-1730). Therefore, the toxicity of dextran could be underestimated.

However, dextran has a higher colloid osmotic pressure than other agents such as albumin or hydroxyethyl starch (Mitra, S., et al., "Are all colloids the same? How to select the right colloid?," *Indian J. Anaesth.*, Wolters Kluwer, Medknow Publications, 2009, 53(5), 592-607), and consequently, corneal stromal hydration could be affected if full-thickness corneal grafts are incubated in dextran-free media, especially in hypothermia.

Ideally, corneal grafts should be preserved using specific media that maintain corneal endothelial cells in optimum conditions and prevent corneal stromal swelling. Unfortunately, the use of one single medium to preserve corneal grafts is an important limiting factor. Current storage vials allow the corneal graft tissue to be preserved in only a single medium that bathes the entire cornea, and therefore, it is not possible to customize it for each corneal layer.

Further, conventional corneal transplant preparation requires that the eye bank technician view the corneal graft tissue with two different types of microscopes. It is, understandably, not desirable to remove the corneal graft tissue from the storage container for this inspection, because of the risks associated with exposing the tissue to a non-sterile environment. Thus, the container (or vial) used to hold the corneal graft tissue is typically constructed to facilitate such inspection directly through the container without necessitating the removal of the corneal graft tissue from the container. In this case, the container is typically referred to as a "viewing chamber." The technician uses a slit-lamp microscope to check for evidence of any corneal graft abnormality and then uses a specular microscope to verify that the proportion of living endothelial cells is adequate to ensure a successful transplant.

SUMMARY

Some embodiments advantageously provide devices and a method for preserving corneal graft tissue. In one embodiment, a device for preserving corneal graft tissue comprises: a first chamber; a second chamber; and a corneal graft tissue suspension assembly that is configured to retain and suspend the corneal graft tissue between the first chamber and the second chamber such that the first chamber is fluidly isolated from the second chamber.

In one aspect of the embodiment, the corneal graft tissue suspension assembly includes: a first element; and a second element, the first element and the second element being vertically and horizontally aligned with each other when the device is assembled, the corneal graft tissue suspension assembly being configured to retain and suspend the corneal graft tissue between at least a portion of the first element and at least a portion of the second element.

In one aspect of the embodiment, the device includes a gap between the first element and the second element when the device is assembled. In one aspect of the embodiment, the gap is between approximately 0.25 mm and approximately 0.85 mm.

In one aspect of the embodiment, the first element includes a corneal graft tissue support structure defining a first aperture; and the second element includes a corneal graft tissue retainment structure defining a second aperture, the first and second apertures being configured to be vertically and horizontally aligned when the device is assembled.

In one aspect of the embodiment, the device further comprises: a first portion; a second portion that is removably couplable to the first portion, the first portion and the second portion together defining the first chamber; a third portion that is removably couplable to the second portion; and a lid that is removably couplable to the third portion, the lid, the third portion, and at least a portion of the third portion together defining the second chamber. In one aspect of the embodiment, the second portion includes a first element of the corneal graft tissue suspension assembly and the third portion includes a second element of the corneal graft tissue suspension assembly.

In one aspect of the embodiment, the device further comprises a longitudinal axis extending from the first portion to the lid, the first element of the corneal graft suspension assembly including an at least substantially planar portion that lies in a plane that is at orthogonal to the longitudinal axis.

In one aspect of the embodiment, the device further comprises a longitudinal axis extending from the first portion to the lid, the second element of the corneal graft suspension assembly lying in a plant that is orthogonal to the longitudinal axis. In one aspect of the embodiment, the third portion includes an annular body portion, the second element of the corneal graft suspension assembly including: an annular structure defining a central aperture; and a plurality of radial spokes extending between the annular structure and an inner surface of the annular body portion, the central aperture being coaxial with the annular body portion and the annular body portion partially defining the second chamber.

In one aspect of the embodiment, the first portion includes at least one first tab; the second portion includes at least one first slot and at least one second tab, the at least one first slot being configured to matingly accept the at least one first tab; the third portion includes at least one second slot and at least one third tab, the at least one second slot being configured to matingly and removably accept the at least one second tab; and the lid includes at least one third slot, the at least one third slot being configured to matingly and removably accept the at least one third tab.

In one aspect of the embodiment, the at least one first tab includes two first tabs that are positioned approximately 180° from each other; the at least one first slot includes two first slots that are positioned approximately 180° from each other; the at least one second tab includes two second tabs that are positioned approximately 180° from each other and are vertically aligned with the two first slots; the at least one second slot includes two second slots that are positioned approximately 180° from each other; the at least one third tab includes two third tabs that are positioned approximately 180° from each other and are horizontally aligned with the two second slots; and the at least one third slot includes two third slots that are positioned approximately 180° from each other.

In one aspect of the embodiment, the device further comprises a longitudinal axis, each of the at least one second slot and the at least one third slot including a release element, each release element including a grip portion that extends away from the longitudinal axis.

In one embodiment, a method of preserving corneal graft tissue within a vial, the corneal graft tissue having an endothelial side and an epithelial side opposite the endothelial side, comprises: coupling a first portion of the vial to a second portion of the vial to create a first chamber therebetween, the second portion of the vial including a corneal graft tissue support structure having an aperture; filling the first chamber with a first preservation medium; placing the corneal graft tissue within a corneal graft tissue support structure and over the aperture such that at least a first portion of the epithelial side is in contact with the corneal graft tissue support structure and at least a second portion of the epithelial side is in contact with the first preservation medium through the aperture; coupling a third portion of the vial to the second portion of the vial, the third portion of the vial including a corneal graft tissue retainment structure, such that the corneal graft tissue is retained between the corneal graft tissue support structure of the second portion of the vial and the corneal graft tissue retainment structure of the third portion of the vial and a second chamber is defined between the corneal graft tissue support structure, the corneal graft tissue, and the third portion of the vial; filling second chamber with a second preservation medium, such that the second preservation medium contacts the endothelial side and the first chamber and the second chamber are fluidly isolated from each other; and coupling a lid to the third portion of the vial.

In one aspect of the embodiment, the first preservation medium is an epithelial preservation medium and the second preservation medium is an endothelial preservation medium.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
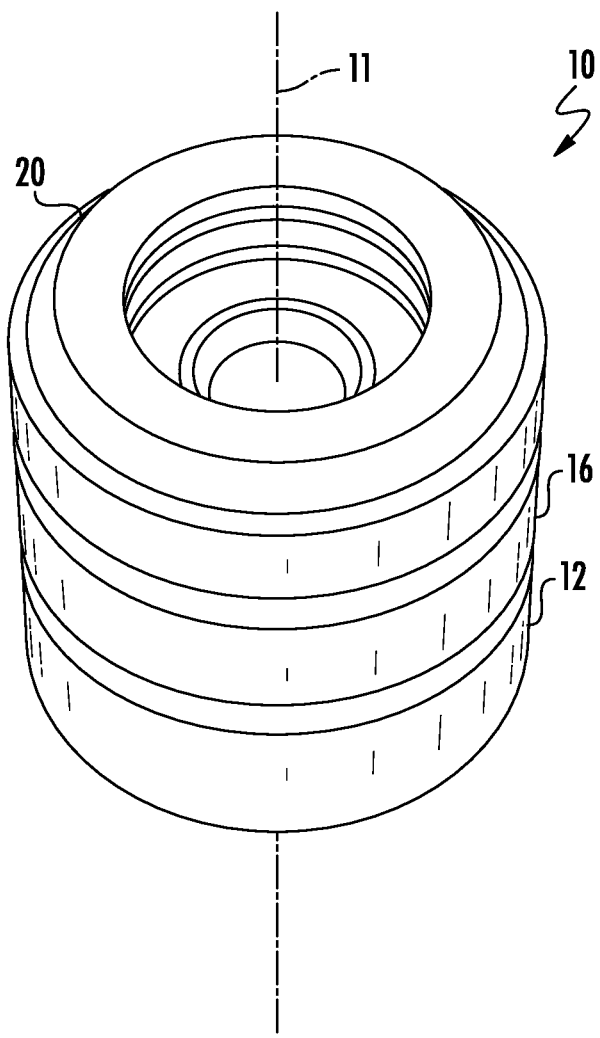
FIG. 1 shows a top perspective view of a first embodiment of an assembled dual-chamber vial, in accordance with the present disclosure.

Before describing in detail exemplary embodiments, it is noted that the embodiments reside primarily in combinations of apparatus components and processing steps related to storing and preserving corneal graft tissue. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 2:
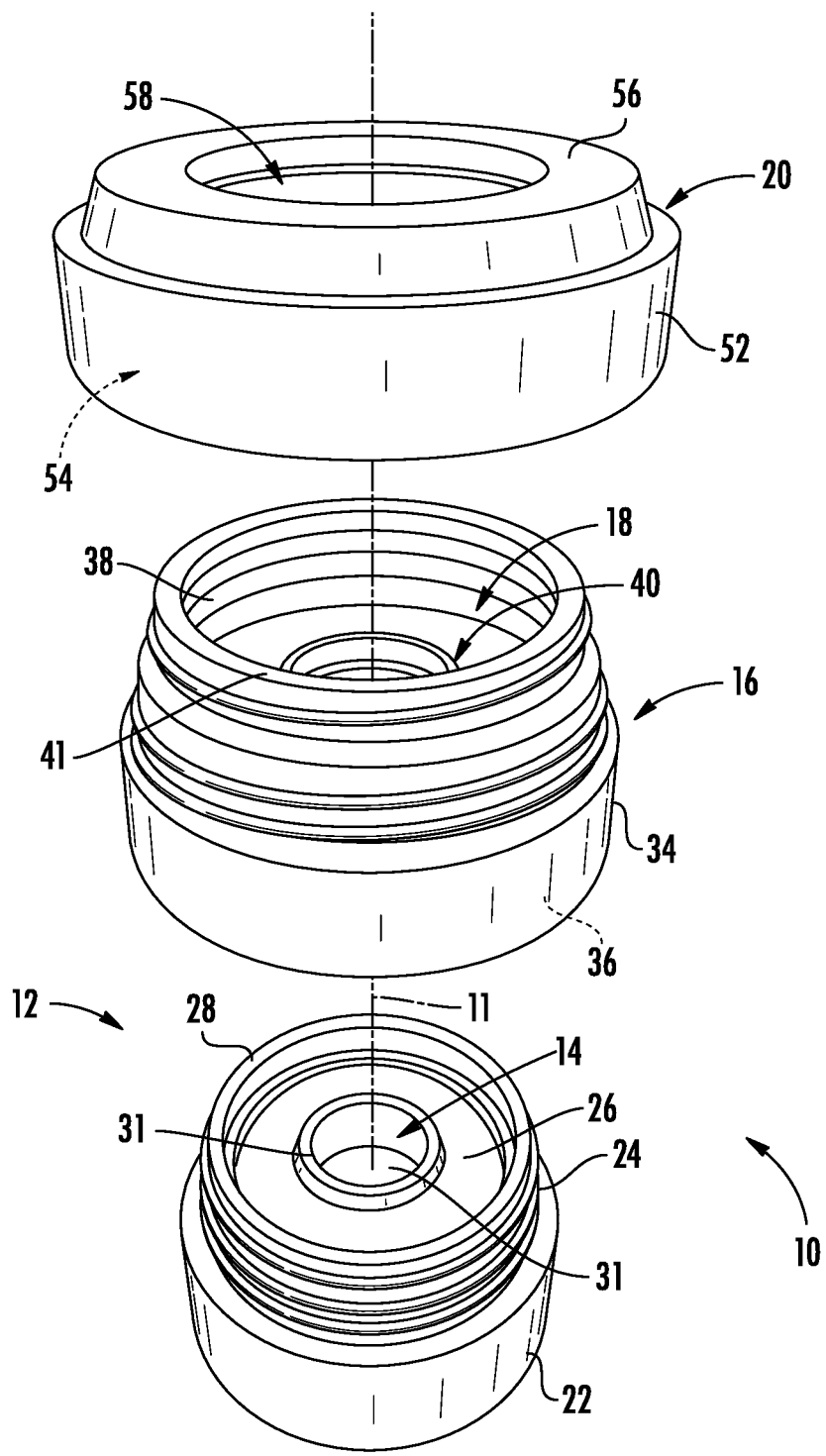
FIG. 2 shows an exploded view of the dual-chamber vial of FIG. 1, in accordance with the present disclosure.
Figure 3:
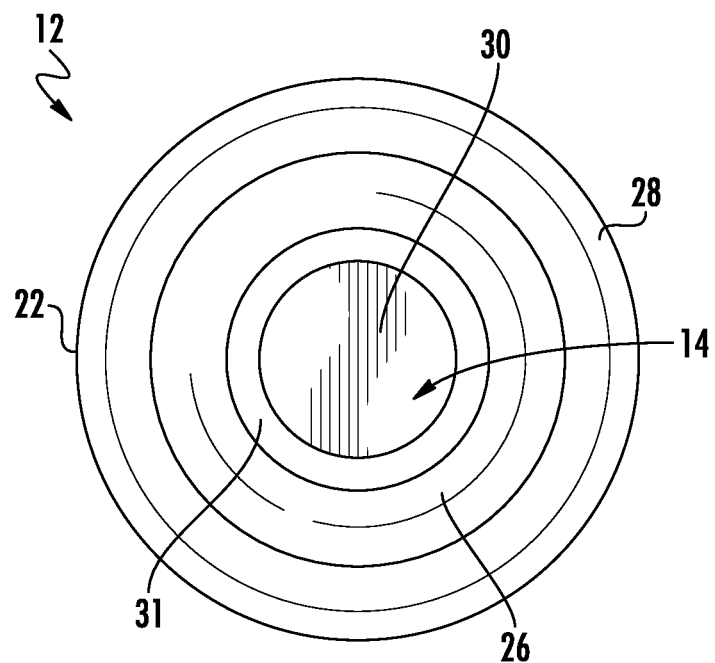
FIG. 3 shows a top view of a lower or first portion of the dual-chamber vial of FIG. 1, in accordance with the present disclosure.
Figure 4:
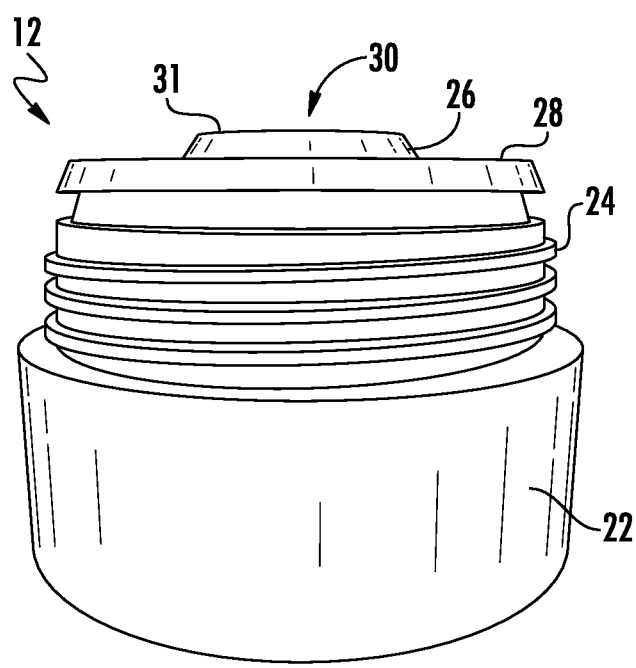
FIG. 4 shows a side view of the lower or first portion of FIG. 3, in accordance with the present disclosure.
Figure 5:
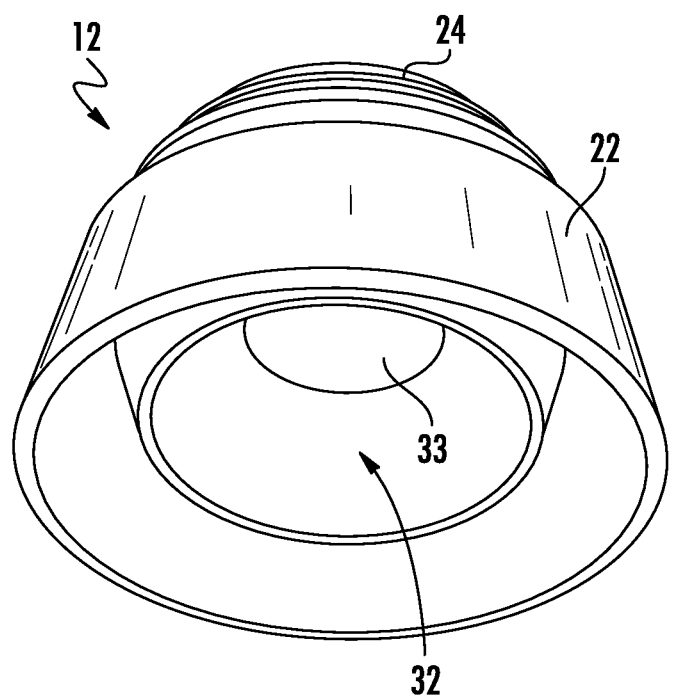
FIG. 5 shows a bottom perspective view of the lower or first portion of FIG. 3, in accordance with the present disclosure.
Figure 6:
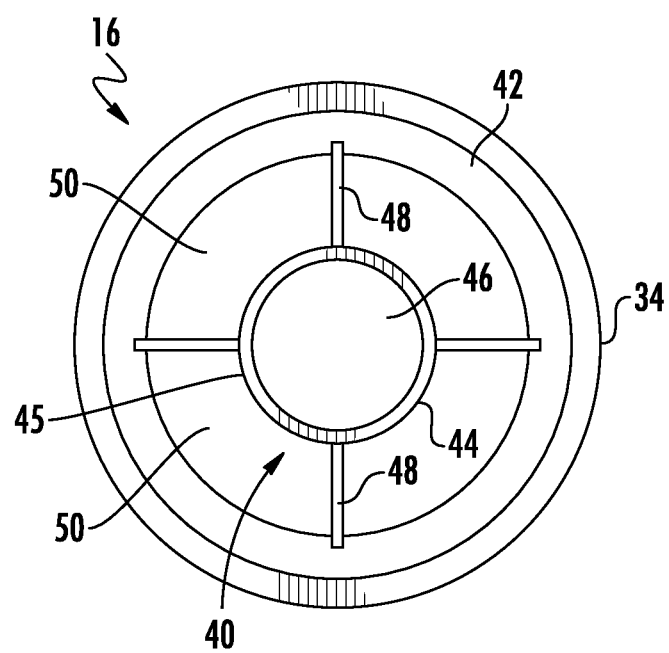
FIG. 6 shows a top view of an upper or second portion of the dual-chamber vial of FIG. 1, in accordance with the present disclosure.
Figure 7:
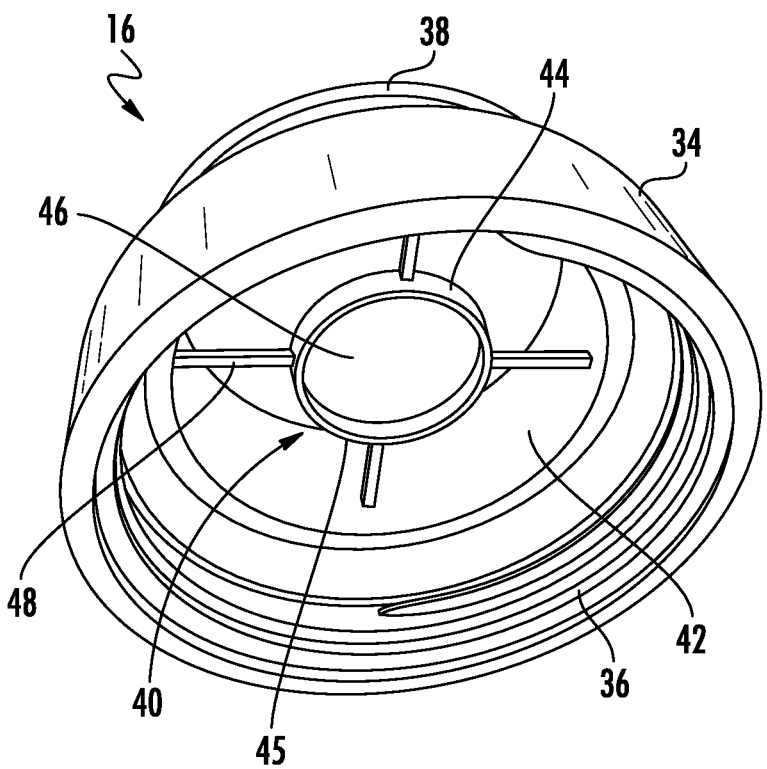
FIG. 7 shows a bottom perspective view of the upper or second portion of FIG. 6, in accordance with the present disclosure.
Figure 8:
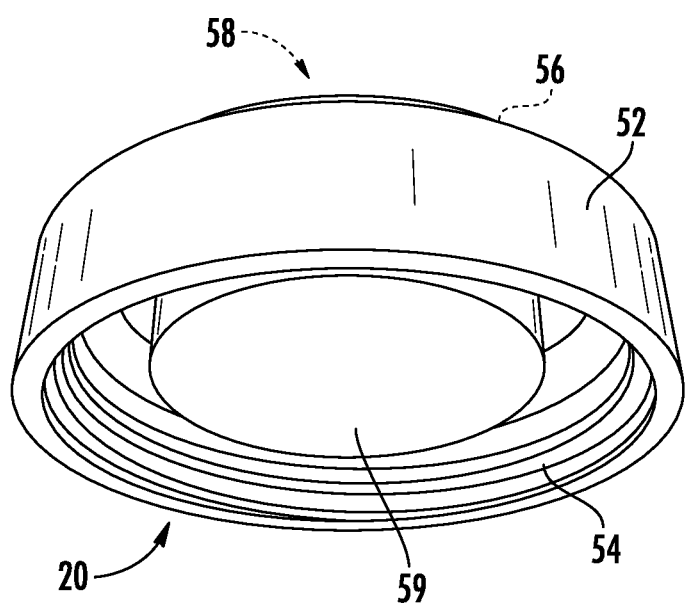
FIG. 8 shows a bottom perspective view of a lid of the dual-chamber vial of FIG. 1, in accordance with the present disclosure.

Referring now to FIGS. 1-8, a first embodiment of a device for storing and preserving corneal graft tissue is shown. In one embodiment, the device is a dual-chamber vial. FIG. 1 shows a top perspective view of the first embodiment of an assembled dual-chamber vial, FIG. 2 shows an exploded view thereof, FIG. 3 shows a top view of a lower or first portion thereof, FIG. 4 shows a side view of the lower or first portion, FIG. 5 shows a bottom perspective view of the lower or first portion, FIG. 6 shows a top view of an upper or second portion of the first embodiment of the dual-chamber vial, FIG. 7 shows a bottom view thereof, and FIG. 8 shows a bottom perspective view of a lid of the first embodiment of the dual-chamber vial.

Ideally, corneal graft tissue storage preservation media should maintain both epithelial and endothelial viability during prolonged storage and prevent corneal stromal swelling. The dual-chamber vial disclosed herein allows the preservation of corneal graft tissue (for example, human corneal graft tissue) using, in one embodiment, two different media simultaneously (that is, a first preservation medium/media in the first chamber and a second preservation medium/media in the second chamber). Therefore, the corneal graft tissue is incubated using the most appropriate preservation medium or media for corneal epithelial cells on one side and a different most appropriate preservation medium or media for corneal endothelial cells on the other side. In another embodiment, the same preservation medium (or combination of preservation media) is used in the first and second chambers. However, as the first and second chambers are fluidly isolated from each other when the dual chamber vial is assembled and a corneal graft tissue is within, both the epithelial side and the endothelial side are well preserved. For example, epithelial cells typically die faster than endothelial cells and, as this occurs, they release cellular contents that may be damaging to endothelial cells. Keeping the medium/media in the first chamber fluidly isolated (that is, separated) from the medium/media in the second chamber, even if the media are the same, will prevent cellular contents and factors from the epithelial side from coming into contact with the endothelial side of the corneal graft tissue As each corneal layer is optimally preserved, the cornea graft tissue may be stored for a longer period of time with no or minimal degradation. In one non-limiting example, the dual-chambered vial is configured to allow a corneal graft tissue to be stored therein such that a first preservation medium or mixture of media (in one embodiment, an epithelial preservation medium and, in one non-limiting example, one or more dextran-containing media) in in a first chamber and in contact with the epithelial side of the corneal graft tissue and a second preservation medium or mixture of media (in one embodiment, an endothelial preservation medium and, in one non-limiting example, one or more low-dextran or dextran-free media) is in a second chamber and in contact with the endothelial side of the corneal graft tissue. However, as noted above, it will be understood that any media may be used in the dual-chamber vial, including the same medium or mixture of media in both the first chamber and the second chamber. Further, the corneal graft tissue is secured within the dual chamber vial such that the two preservation media are fluidly isolated from each other and do not mix. Thus, the dual chamber vial may maintain the endothelial cell viability over time by isolating the endothelial cells from the dextran-containing media. However, it will also be understood that other media than those described herein may be used in one or both chambers of the dual-chamber vial. The dual-chamber vial may be composed of any suitable non-porous material, such as plastic, and may be disposable or reusable (in which case, the dual-chamber vial may be composed of a material that can be sterilized without degradation). Further, in one embodiment, the material from which the dual-chamber vial is composed is transparent and/or translucent to facilitate viewing of the corneal graft tissue by the naked eye and/or a microscope when the corneal graft tissue is within the dual-chamber vial. For simplicity, however, the dual-chamber vial may appear opaque in the figures to simplify depiction of its structure.

Referring now to FIG. 1, in one embodiment, the dual-chamber vial 10 generally includes a longitudinal axis 11, a lower or first portion 12 defining a lower or first chamber 14, an upper or second portion 16 that at least partially defines an upper or second chamber 18, and a lid 20 that at least partially defines the second chamber 18. Thus, the dual-chamber vial 10 is generally composed of three components that are removably couplable to each other. In one embodiment, the dual-chamber vial 10 has a generally cylindrical shape, with flat or at least substantially flat ends (or at least a portion of each end is flat, allowing the dual-chamber vial 10 to securely stand or rest on a flat surface) and a round cross-sectional shape. In this configuration, one end of the dual-chamber vial 10 may be set on a flat surface such that the second portion 16 is above and vertically aligned with the first portion 12. As shown in FIG. 2, the first portion 12, second portion 16, and lid 20 each have at least one threaded areas by which the dual-chamber vial 10 is assembled. Further, as is described in more detail below, each of the first portion 12 and the second portion 16 includes a corneal graft tissue engagement feature that positions and suspends the corneal graft tissue within the dual-chamber vial 10 such that a first preservation medium within the first chamber 14 is in contact with the epithelial side of the corneal graft tissue and a second preservation medium within the second chamber 18 is in contact with the endothelial side of the corneal graft tissue. In one embodiment, each of the first portion 12, the second portion 16, and the lid 20 have the same or substantially the same outer diameter, so the assembled dual-chamber vial 10 is a continuous or at least substantially continuous outer diameter. However, it will be understood that the assembled dual-chamber vial 10, and/or components thereof, may have different sizes, shapes, and configurations than those shown and described herein.

Figure 9:
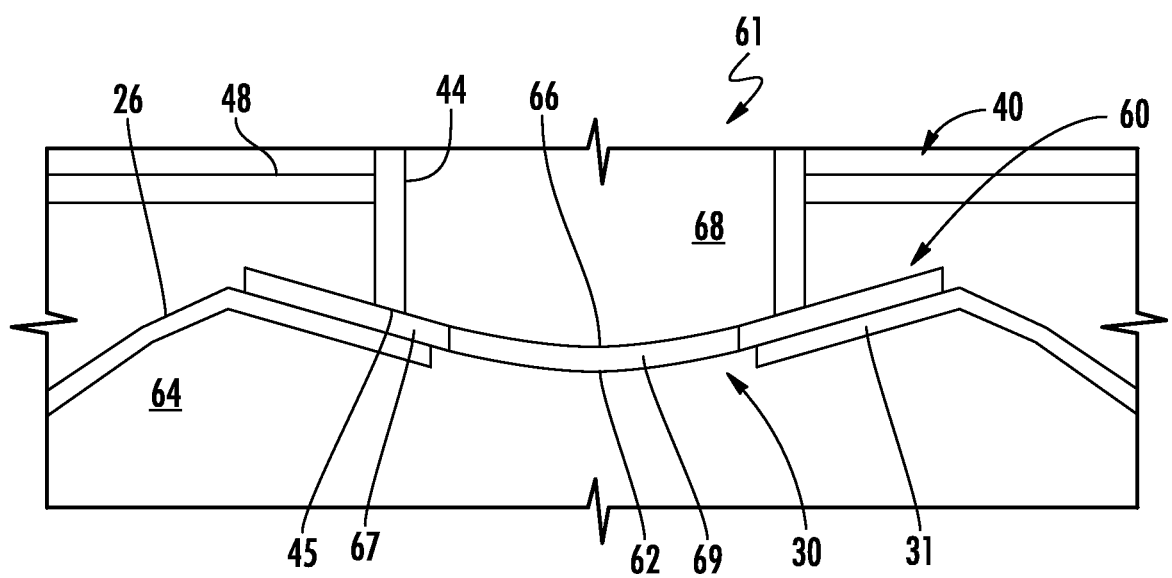
FIG. 9 shows a simplified cross-sectional view of at least a portion of corneal graft tissue within a corneal graft suspension assembly of the dual-chamber vial of FIG. 1, in accordance with the present disclosure.

Referring now to FIGS. 2-5, the first portion 12 is shown in greater detail. In one embodiment, the first portion 12 generally includes a base 22, threading 24 on an outer surface of the first portion 12, and a corneal graft tissue support structure 26. In one embodiment, the threading 24 is immediately adjacent to (for example, above) the base 22 and defines a rim 28. Further, in one embodiment, the corneal graft tissue support structure 26 is a convex or at least substantially convex element that defines an aperture 30. The aperture 30 may be a central aperture (as shown in FIG. 3) or may be at other locations in the corneal graft tissue support structure 26. The corneal graft tissue support structure 26 may generally have a convex configuration (oriented toward the second portion 16, or away from the first chamber 14). In some embodiments, the first chamber 14 is defined by the base 22 and/or threading 24 (on the bottom and sides) and the corneal graft tissue support structure 26 (on the top), with the aperture 30 being in communication with or opening into the first chamber 14. The corneal graft tissue support structure 26 also includes a generally concave or bowl-shaped engagement rim 31 surrounding, or at least partially surrounding, the aperture 30. In one embodiment, the engagement rim 31 circumscribes the aperture 30 and has a curvature that is opposite the general curvature of the corneal graft tissue support structure 26, with the engagement rim 31 being angled toward the first chamber 14. As shown in FIG. 9, the concave configuration of the engagement rim 31 cradles or supports the corneal graft tissue in its normal concave configuration, with the epithelial side of the corneal graft tissue facing the first chamber 14 and the endothelial side of the corneal graft tissue facing the second chamber 18 (in some embodiments, with the epithelial tissue facing downward and the endothelial tissue facing upward) when the dual-chamber vial 10 is assembled. Epithelial cells die more rapidly than endothelial cells, with a typical epithelial cell lifespan being approximately one week. With the corneal graft tissue being supported such that the epithelial side is facing downward, or toward the first chamber 14, the epithelial cells may freely fall into the first chamber 14 and away from the corneal graft tissue.

Continuing to refer to FIGS. 2-5, in some embodiments, the base 22 defines or includes an indentation 32 (for example, as shown in FIG. 5), and the indentation 32 (and/or the threading 24) and the corneal graft tissue support structure 26 together define the first chamber 14. This indentation 32 at least partially defines the floor or lower surface of the first chamber 14, and provides a viewing surface 33 through which the epithelial side of the corneal graft tissue within the dual-chamber vial 10 can be viewed. Further, at least a portion of the indentation 32 (such as the viewing surface 33) is proximate or closely proximate (for example, within between approximately 0.10 mm and approximately 0.25 mm of, ±0.01 mm) the epithelial side of the corneal graft tissue which further enhances viewability. Additionally, this configuration may be used to reduce the volume of the first chamber 14 and, therefore, an amount of first preservation medium required to adequately preserve at least the endothelial cells of the corneal graft tissue. Optionally, in one embodiment, at least a portion of the corneal graft tissue support structure 26 extends above the rim 28 of the base 22 (for example, as shown in FIG. 4).

Referring now to FIGS. 2, 6, and 7, the second portion 16 is shown in greater detail. In one embodiment, the second portion 16 generally includes an annular body portion 34, a first threading 36, a second threading 38, and a corneal graft tissue retainment structure 40. When the dual-chamber vial 10 is assembled, the corneal graft tissue support structure 26 and the corneal graft tissue retainment structure 40 may together be referred to as the corneal graft tissue suspension assembly. In one embodiment, the first threading is within (that is, on an interior surface of) the annular body portion 34 and the second threading 38 is immediately adjacent (for example, above) the annular body portion 34 and on an outer surface of the second portion 16 (as shown in FIGS. 2 and 7). When the dual-chamber vial 10 is assembled, the threading 24 of the first portion 12 mateably engages with the first threading 36 of the second portion 16. Further, the second threading 38 ends at a rim 41 that extends beyond (that is, above when the dual-chamber vial 10 is assembled) the corneal graft tissue retainment structure 40, thereby at least partially defining the second chamber 18. Thus, when the dual-chamber vial 10 is assembled, the second portion 16, the lid 20, and the corneal graft tissue support structure 26 of the first portion 12 together define, or at least partially define, the second chamber 18.

In one embodiment, such as that shown in FIGS. 6 and 7, the corneal graft tissue retainment structure 40 is coupled to or integrated with an inner surface 42 of the annular body portion 34 and includes an annular structure 44, which defines a central aperture 46, and a plurality of radial spokes 48 extending between the annular structure 44 and the inner surface 42 of the annular body portion 34. Thus, the radial spokes 48 define a plurality of apertures 50 between the annular structure 44 and the inner surface 42 of the annular body portion 34. In one embodiment, the central aperture 46 is aligned along the longitudinal axis 11 with the aperture 30 of the first portion 12. The annular structure 44 includes an engagement rim 45 that is sized and configured to engage or contact the sclera portion of the corneal graft tissue (for example, as shown in FIG. 9). The radial spokes 48 are coupled to or meet the annular structure 44 such that the engagement rim 45 and at least a portion of the annular structure 44 are located closer to the corneal graft tissue support structure 26 than the radial spokes 48. Thus, when the dual-chamber vial 10 is assembled, the radial spokes 48 do not contact or interfere with the corneal graft tissue and, in particular, the peripheral sclera. Optionally, the engagement rim 45 of the annular structure 44 is contoured to follow the natural curvature of the corneal graft tissue (and, in some embodiments, that of the engagement rim 31 of the corneal graft tissue support structure 26).

Continuing to refer to FIGS. 2, 6, and 7, although the corneal graft tissue suspension assembly (26 and 40) may have a convex configuration, the corneal graft tissue suspension assembly generally lies in a plane that is orthogonal to, or at least substantially orthogonal to, the longitudinal axis 11 of the dual-chamber vial 10 (put another way, in one embodiment the corneal graft tissue suspension assembly is configured to support the corneal graft tissue generally in a plane that bisects the dual-chamber vial 10 into a lower chamber 14 and an upper chamber 18). In one embodiment, the corneal graft tissue suspension assembly generally includes a first element, which includes at least the corneal graft tissue support structure 26, and a second element, which includes at least the corneal graft tissue retainment structure 40, and the first and second elements are configured to be vertically and horizontally aligned when the dual-chamber vial 10 is assembled. Further, in one embodiment there is a gap of between approximately 0.25 mm (±0.05 mm) and approximately 0.85 mm (±0.05 mm) between at least a portion of the first element and at least a portion of the second element (for example, between the engagement rims 31 and 45), such that when the dual-chamber vial 10 is assembled and contains a corneal graft tissue, the corneal graft tissue is suspended between, and may be in contact with each of, the corneal graft tissue support structure 26 of the first portion 12 and the corneal graft tissue retainment structure 40 of the second portion 16. In particular, the epithelial side of the corneal graft tissue rests on the corneal graft tissue support structure 26 such that at least a portion of the epithelial side is exposed through the aperture 30 to the preservation medium within the first chamber 14 and at least a portion of the epithelial side is in contact with the engagement rim 31 surrounding the aperture 30. Further, when the dual-chamber vial 10 is assembled, the engagement rim 45 of the annular structure 44 of the corneal graft tissue retainment structure 40 circumscribes, but is not in contact with, the endothelial side of the cornea, but is in contact with (or closely proximate) the sclera (for example, the endothelial side of the sclera), as shown in FIG. 9. Thus, the cornea of the corneal graft tissue may be protected from damage while in storage.

Referring now to FIGS. 2 and 8, the lid 20 is shown in greater detail. In one embodiment, the lid 20 generally includes a body portion 52 that includes a threading 54 on an inner surface. When the dual-chamber vial 10 is assembled, the lid 20 and the second portion 16, or at least the part of the second portion 16 that is above the location of the corneal graft tissue, together define the second chamber 18. In one embodiment, the lid 20 also includes a face 56 and an indentation 58 that extends from the face 56 and into the dual-chamber vial 10 toward the second portion 16 (for example, downward when the dual-chamber vial 10 is assembled). The indentation 58 at least partially defines the roof or upper surface of the second chamber 18 and provides a viewing surface 59 through which the endothelial side of a corneal graft tissue within the dual-chamber vial 10 can be viewed. Further, at least a portion of the indentation 58 (such as the viewing surface 59) is proximate or closely proximate (for example, within between approximately 0.10 mm and approximately 0.25 mm of, ±0.01 mm) the endothelial side of the corneal graft tissue, which further enhances viewability. In one embodiment, the indentation 58 is sized and configured to receive at least a portion of a microscope lens or other viewing or imaging device. Additionally, this configuration may be used to reduce the volume of the second chamber and, therefore, an amount of second preservation medium required to adequately preserve at least the epithelial cells of the corneal graft tissue.

Referring again to FIGS. 1-8, it will be understood that each component of the dual-chamber vial 10 is sized and configured to facilitate assembly and prevent damage to the corneal graft tissue within. That is, the threading depth, spacing, and outer diameter of the threadings 24 and 36 are configured so the first portion 12 and the second portion 16 are mateably and removably engageable with each other, and the threading depth, spacing, and outer diameter of the threadings 38 and 54 are configured to the second portion 16 and the lid 20 are mateably and removably engageable with each other. Further, the threadings 24 and 36 are configured such that when the second portion 16 is screwed tightly to the first portion 12 and further tightening rotation of the first portion 12 and/or second portion 16 is not possible, there is a small gap between the corneal graft tissue support structure 26 and the corneal graft tissue retainment structure 40. In one non-limiting example, if the corneal graft tissue is from a human cornea, the dual-chamber vial 10 may be configured such that the gap is between approximately 0.25 mm (±0.05 mm) and approximately 0.85 mm (±0.05 mm). Thus, the corneal graft tissue is not damaged by overtightening of the dual-chamber vial 10 during assembly.

Referring now to FIG. 9, a simplified cross-sectional view of at least a portion of corneal graft tissue 60 within a corneal graft tissue suspension assembly 61 is shown. As is described above, when the corneal graft tissue is within the dual-chamber vial 10, the corneal graft tissue is retained and suspended within the corneal graft tissue suspension assembly 61 such that the epithelial side 62 is in contact with the engagement rim 31 of the corneal graft tissue support element 26 and the first preservation medium (or media) 64 within the first chamber 14 and the endothelial side 66 is in contact with the engagement rim 45 of the annular structure 44 of the corneal graft tissue retainment structure 40 and the second preservation medium (or media) 68 within the second chamber 18. Further, in one embodiment the engagement rim 45 is in contact with the endothelial side 66 of the sclera 67, and not the endothelial side 66 of the cornea 69. As noted above, FIG. 9 shows at least a portion of corneal graft tissue 60 within the corneal graft tissue suspension assembly 61, and it will be understood that corneal graft tissue 60, and the corneal graft tissue suspension assembly 61, may be wider and/or sized and configured differently than that shown in FIG. 9.

Figure 10:
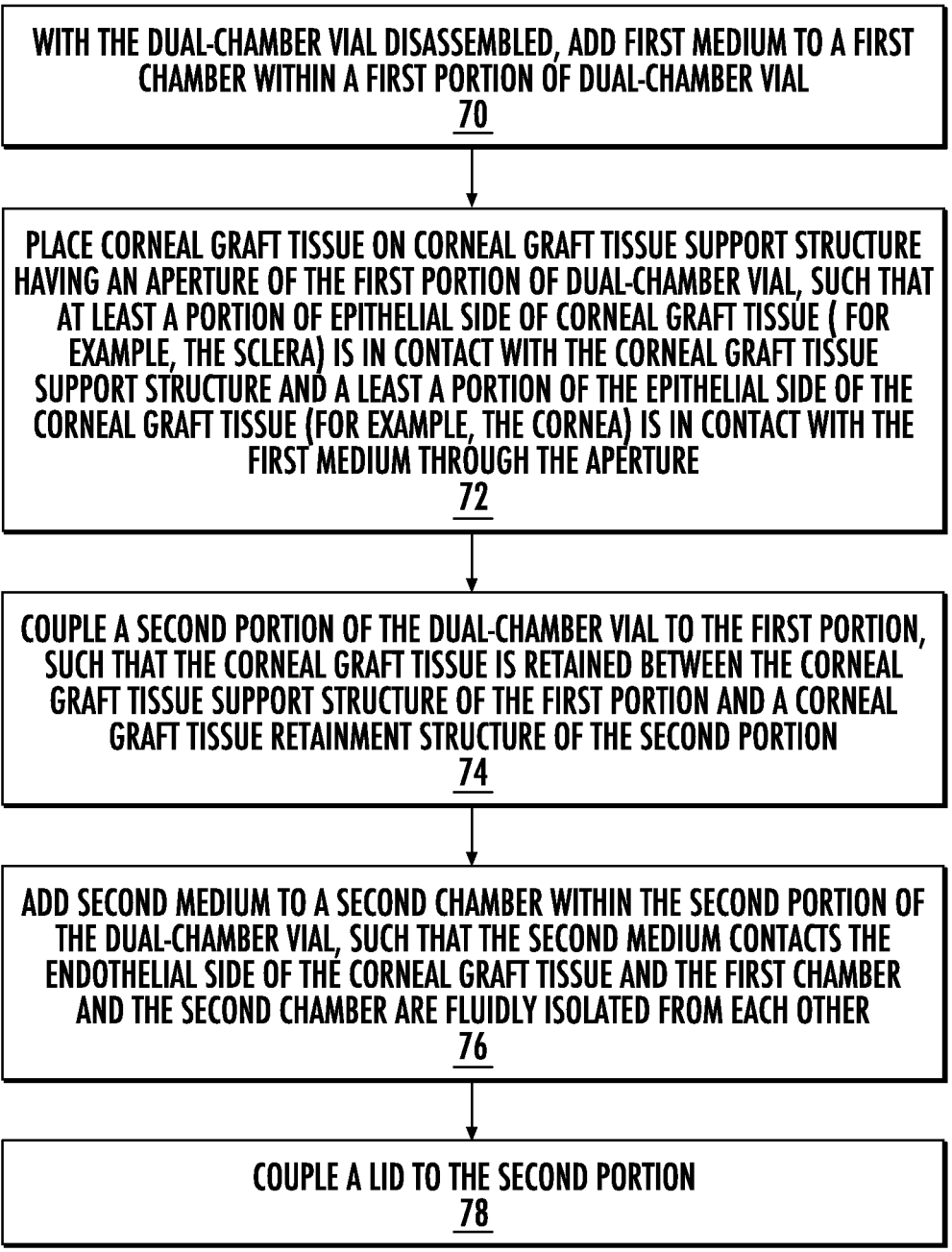
FIG. 10 shows a flow chart of an exemplary method for storing and preserving corneal graft tissue within the dual-chamber vial of FIG. 1, in accordance with the present disclosure.

Referring now to FIG. 10, a flow chart of an exemplary method for storing and preserving corneal graft tissue 60 within the dual-chamber vial 10 is shown. In a first step 70, with the dual-chamber vial 10 disassembled, a first preservation medium (or mixture of media) 64 is added to the first chamber 14, such as through the aperture 30 in the corneal graft tissue support structure 26, until the level of the first preservation medium 64 is level with or immediately proximate the aperture 30. In one non-limiting example, the first portion 12 is sized and configured such that approximately 10 mL of the first preservation medium 64 may be added to the first chamber 14. However, it will be understood that the dual-chamber vial 10 may be sized and configured to hold any amount of preservation medium.

Continuing to refer to FIG. 10, in a second step 72, corneal graft tissue 60 is placed on the corneal graft tissue support structure 26 such that at least a portion of the epithelium 62 (for example, the sclera 67) is in contact with an upper surface of the engagement rim 31 of the corneal graft tissue support structure 26 and at least a portion of the epithelium 62 (for example, the corneal epithelium 69) is in contact with the first preservation medium 64 through the aperture 30. In a third step 74, once the corneal graft tissue 60 is in place, the second portion 16 is coupled to the first portion 12. For example, the second portion 16 may be screwed onto the first portion 12 (that is, the first threading 36 of the second portion mateably engages with the threading 24 of the first portion 12). Further, when the second portion 16 is coupled to the first portion 12, the engagement rim 45 may be in contact with the endothelial side 66 of the sclera 67, but not the endothelial side 66 of the cornea 69. Thus, the corneal graft tissue 60 is suspended, retained, or otherwise engaged within the dual-chamber vial 10 between the corneal graft tissue support structure 26 and the corneal graft tissue retainment structure 40, and further movement (for example, "sloshing" within the dual-chamber vial 10) of the corneal graft tissue is prevented. Likewise, in some embodiments the corneal graft tissue 60 blocks at least the apertures 30 and 46 to form a fluid-tight seal between the first portion 12 and the second portion 16 and fluidly isolate the first chamber 14 from the second chamber 18.

Continuing to refer to FIG. 10, in a fourth step 76, a second preservation medium 68 (or mixture of media) is added to the second chamber 18, or the portion of the second chamber 18 defined by the second portion 16 (the area between the corneal graft tissue retainment structure 40 and the rim 41). In one non-limiting example, the second portion 16 is sized and configured such that approximately 10 mL of the second preservation medium 68 may be added to the second chamber 18. However, it will be understood that the dual-chamber vial 10 may be sized and configured to hold any amount of medium. Further, the second preservation medium 68 may be optimally suited for preserving endothelial tissue 66. In one embodiment, the second preservation medium 68 is a low-dextran or dextran-free medium. In one embodiment, the second preservation medium 68 flows downward through the apertures 46 and 50 of the corneal graft tissue retainment structure 40 to come into contact with the endothelium 66 of the corneal graft tissue 60, but is prevented from flowing past the corneal graft tissue 60 and into the first chamber 14 or otherwise contacting the epithelium 62 of the corneal graft tissue 60.

Continuing to refer to FIG. 10, in a fifth step 78, the lid 20 is coupled to the second portion 16. For example, the lid 20 may be screwed onto the second portion 16 (that is, the threading 54 of the lid 20 mateably engages with the second threading 38 of the second portion) to fluidly seal the second chamber 18. After this step 78, the dual-chamber vial 10 is fully assembled and fluidly sealed, with the corneal graft tissue 60 safely within. The dual-chamber vial 10 may then be transported and/or stored using any suitable conditions. Further, the epithelial side 62 and/or the endothelial side 66 of the corneal graft tissue 60 may be visualized through the dual-chamber vial 10 (for example, through one or both of the viewing surfaces 33 and 59) with the naked eye and/or a viewing device. To remove the corneal graft tissue 60 from the dual-chamber vial 10, the lid 20 is uncoupled from the second portion 16, the second preservation medium 68 removed or poured out, and then the second portion 16 is uncoupled from the first portion 12 and the exposed corneal graft tissue 60 may be removed and used.

Figure 11:
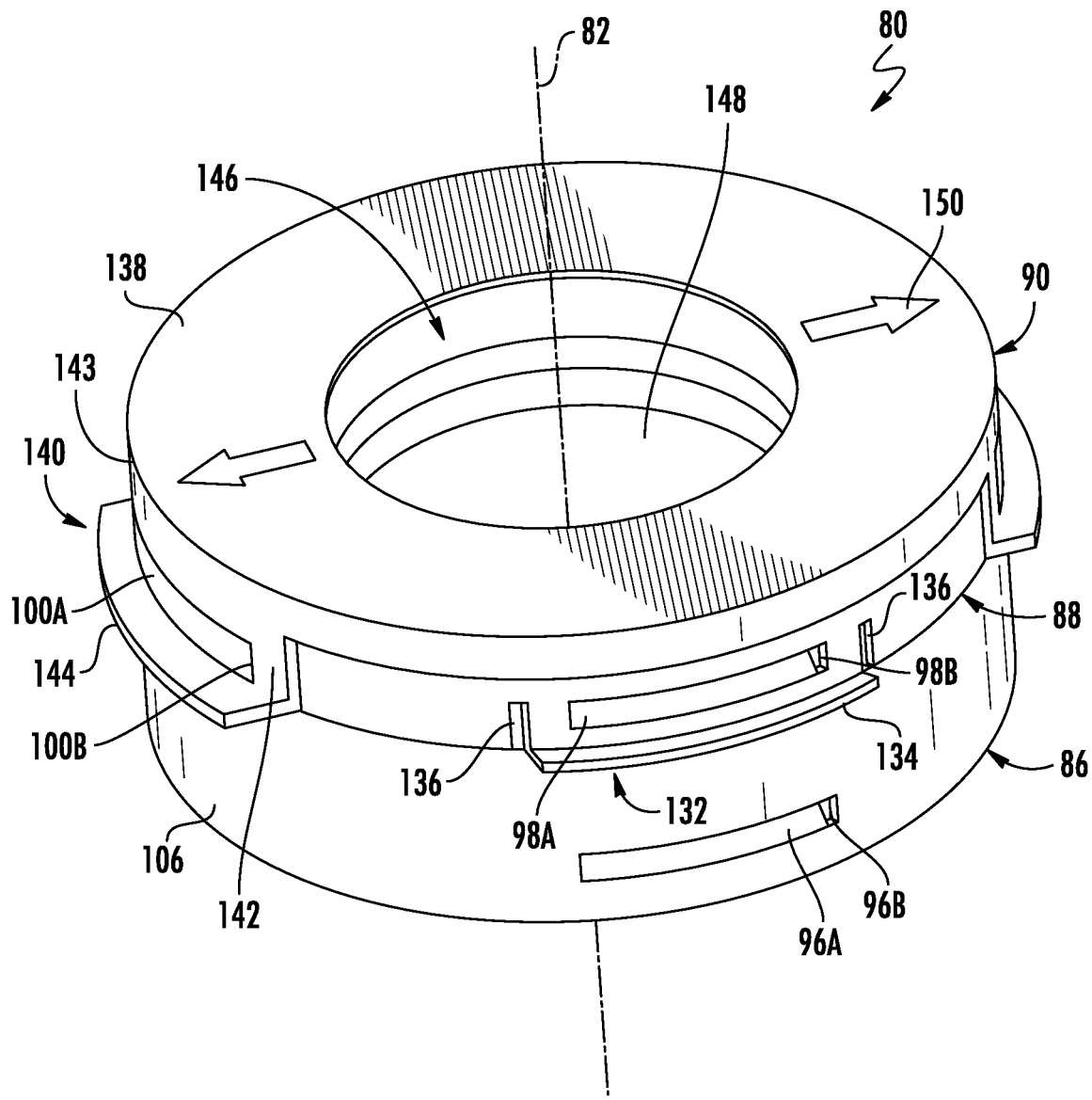
FIG. 11 shows a top perspective view of a second embodiment of an assembled dual-chamber vial, in accordance with the present disclosure.
Figure 12:
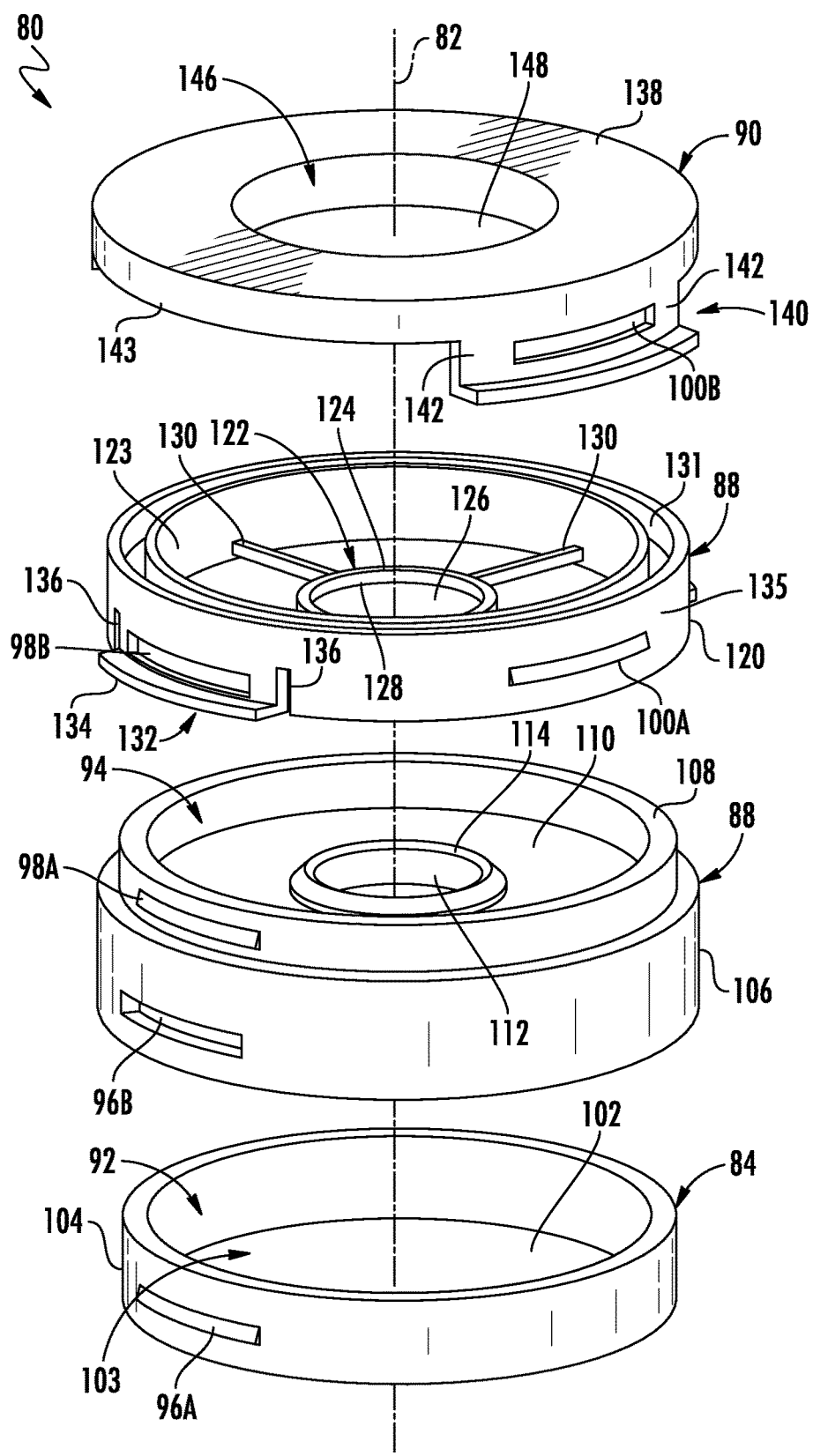
FIG. 12 shows an exploded view of the dual-chamber vial of FIG. 11, in accordance with the present disclosure.
Figure 13:
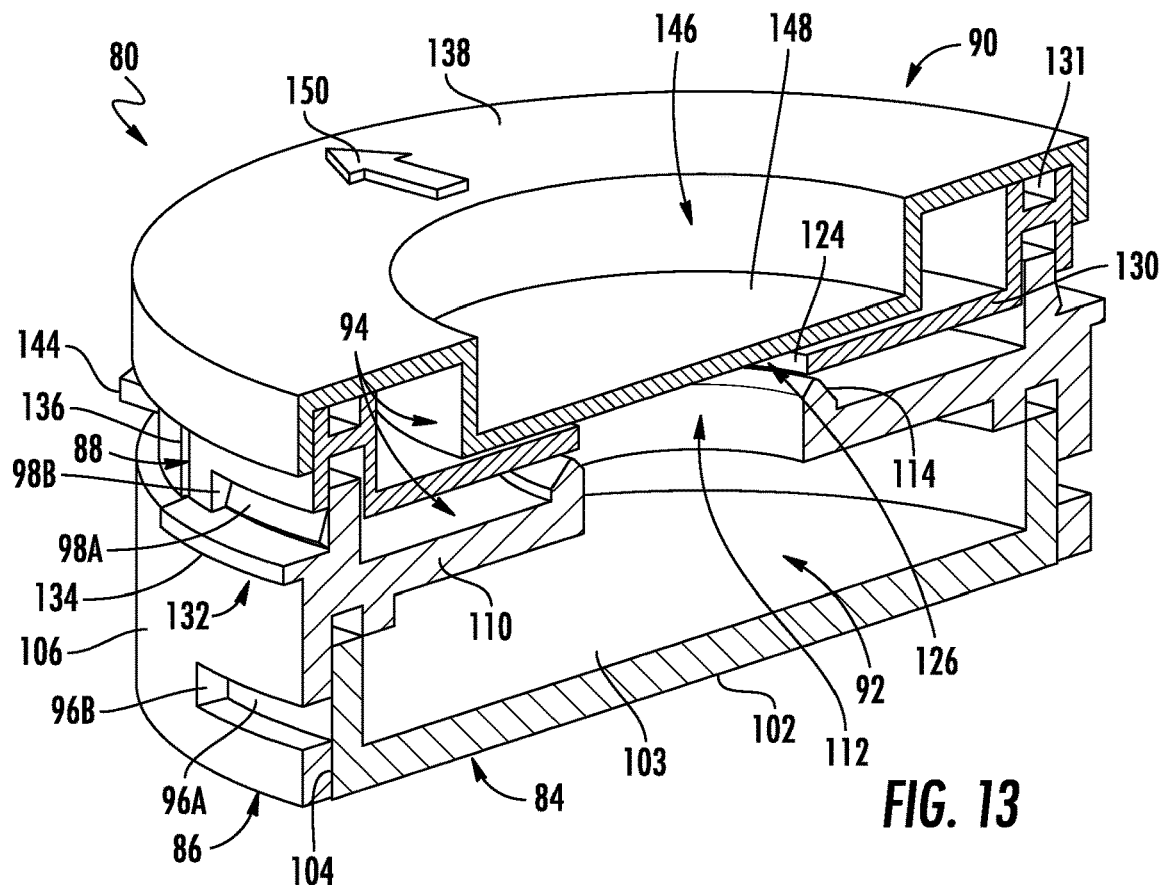
FIG. 13 shows a first cross-sectional view of the dual-chamber vial of FIG. 11, in accordance with the present disclosure.
Figure 14:
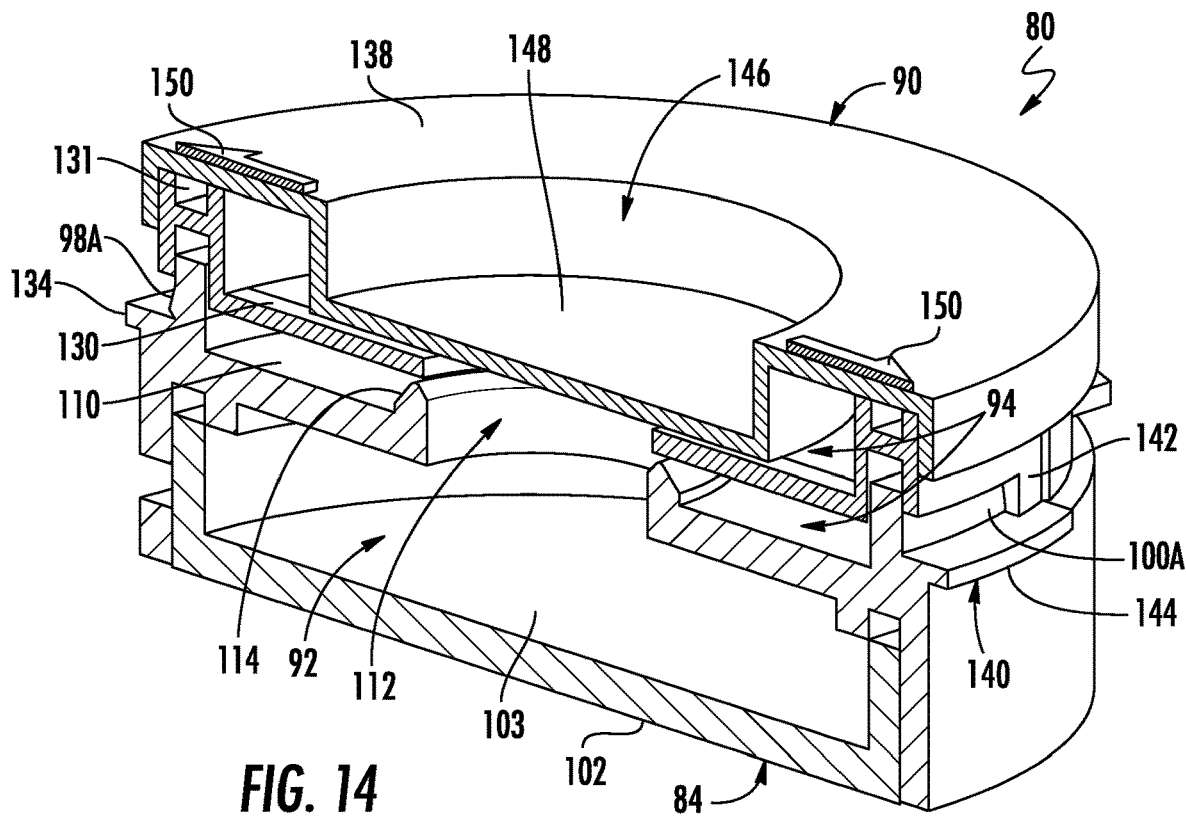
FIG. 14 shows a second cross-sectional view of the dual-chamber vial of FIG. 11 in accordance with the present disclosure.

Referring now to FIGS. 11-14, a second embodiment of device for storing and preserving corneal graft tissue is shown. In one embodiment, the device is a dual-chamber vial. FIG. 11 shows a top perspective view of the second embodiment of an assembled dual-chamber vial, FIG. 12 shows an exploded view thereof, FIG. 13 shows a first cross-sectional view thereof, and FIG. 14 shows a second cross-sectional view thereof. The second embodiment of the dual-chamber vial 80 provides the same functionality as the first embodiment of the dual-chamber vial 10. However, in the second embodiment, the dual-chamber vial 80 is composed of four components that are removably couplable to each other, rather than three components (for example, as shown in FIG. 2). Further, in one embodiment, the second embodiment of the dual-chamber vial 80 includes locking elements rather than threading. However, in another embodiment, the second embodiment of the dual-chamber vial 80 includes threading as shown and described regarding the first embodiment of the dual-chamber vial 10 in FIGS. 1-8. These features of the second embodiment of the dual-chamber vial 80 may simplify manufacturing (for example, each of the four components may be formed by injection molding). Therefore, unless otherwise noted, reference in FIGS. 11-15 to the same features of the first embodiment of the dual-chamber vial 10 of FIGS. 1-10 will be understood to have the same or substantially similar structure and/or function and, to avoid redundancy and complexity, will not be explained in detail regarding FIGS. 11-15.

Continuing to refer to FIGS. 11-14, in one embodiment, the dual-chamber vial 80 generally includes a longitudinal axis 82, a first lower or first portion 84, a second lower or second portion 86, an upper or third portion 88, and a lid 90. In one embodiment, the first portion 84 and the second portion 86, when coupled together, define a first chamber 92 (for example, similar to the first chamber 14 defined by the first portion 12 of the first embodiment of the dual-chamber vial 10). Further, when the dual-chamber vial 80 is assembled, the second portion 86, the third portion 88, and the lid 90 together define a second chamber 94 (for example, similar to the second chamber 18 defined by the second portion 16, the lid 20, and the corneal graft tissue support structure 26 of the first portion 12 of the first embodiment of the dual-chamber vial 10). Further, when the corneal graft tissue is retained within the dual-chamber vial 80, the corneal graft tissue 60 may also define at least a portion of the second chamber 94, as the corneal graft tissue 60 prevents the second preservation medium 68 from passing through the aperture 112 of the corneal graft tissue support structure 110 and entering the first chamber 92. As noted above, in one embodiment the first and second portions 84 and 86 together are structurally analogous to the first portion 12 of the first embodiment of the dual-chamber vial 10 of FIGS. 1-8, the third portion 88 is structurally analogous to the second portion 16 of the first embodiment of the dual-chamber vial 10 of FIGS. 1-8, and the lid 90 is structurally analogous to the lid 20 of the first embodiment of the dual-chamber vial 10 of FIGS. 1-8. Thus, the dual-chamber vial 80 is generally composed of three components 84, 86, and 88 that are removably couplable to each other.

In one embodiment, the dual-chamber vial 80 has a generally cylindrical shape, with flat or at least substantially flat ends (or at least a portion of each end is flat, allowing the dual-chamber vial 80 to securely stand or rest on a flat surface) and a round cross-sectional shape. In this configuration, one end of the dual-chamber vial 80 may be set on a flat surface such that the first portion 84, second portion 86, third portion 88, and lid 90 are vertically aligned with each other (as shown in FIG. 11). In one embodiment, each of the first portion 84, the second portion 86, the third portion 88, and the lid 90 have the same or substantially the same outer diameter, so the assembled dual-chamber vial 80 is a continuous or at least substantially continuous outer diameter. However, it will be understood that the assembled dual-chamber vial 80, and/or components thereof, may have different sizes, shapes, and configurations than those shown and described herein. Further, in one embodiment, the material from which the dual-chamber vial 80, or at least the first portion 84 and the lid 90, is composed is transparent and/or translucent to facilitate viewing of the corneal graft tissue by the naked eye, a microscope, and/or or other viewing device when the corneal graft tissue is within the dual-chamber vial 10. For simplicity, however, the dual-chamber vial may appear opaque in the figures to simplify depiction of its structure.

Continuing to refer to FIGS. 11-14, in one embodiment the components of the dual-chamber vial 80 are couplable to each other by complementary or matable locking members, rather than threading. In one embodiment, the first portion 84 includes at least one tab 96A and the second portion 86 includes at least one slot 96B that is complementary to the at least one tab 96A of the first portion 84. Put another way, each of the at least one tab 96A of the first portion 84 functions as a male locking member and is matingly received by corresponding one of the at least one slot 96B in the second portion 86, thereby securing the first portion 84 and the second portion 86 together. Likewise, in one embodiment, the second portion 86 also includes at least one tab 98A and the third portion 88 includes at least one slot 98B, each of the at least one tab 98A being matingly received by a corresponding one of the at least one slot 98B. Still further, in one embodiment, the third portion 88 also includes at least one tab 100A and the lid 90 includes at least one slot 100B, each of the at least one tab 100A being matingly received by a corresponding one of the at least one slot 100B.

In one embodiment, each tab 96A, 98A, 100A is integrally formed with its corresponding portion 84, 86, 88 of the dual-chamber vial 80, although in other embodiments the tabs 96A, 98A, 100A may be coupled, adhered, or otherwise attached to the portions 84, 86, 88. Further, it will be understood that the tabs 96A, 98A, 100A and/or the slots 96B, 98B, 100B may be positioned around the circumference of the dual-chamber vial 80 at locations other than those shown in the figures, provided the portions 84, 86, 88 can be positioned relative to each other such that the tabs 96A, 98A, 100A and the slots 96B, 98B, 100B can be engaged with one another to lock the portions together 84, 86, 88 when the dual-chamber vial 80 is assembled.

As is best seen in FIG. 12, in one embodiment the first portion 84 generally includes a base 102 and a wall 104 extending from and circumscribing the base 102, and the at least one tab 96A protrudes from the wall 104. In one embodiment, the at least one tab 96A includes two tabs 96A that are opposite each other (that is, positioned at 180°, or at least 180°±5° from each other). In one embodiment, the base 102 provides a viewing surface 103 through which the epithelial side of the corneal graft tissue 60 within the dual-chamber vial 80 can be viewed.

As is best seen in FIG. 12, in one embodiment, the second portion 86 generally includes a wall 106, a rim 108, a corneal graft tissue support structure 110 defining an aperture 112, and an engagement rim 114 surrounding, or at least partially surrounding (or, in some embodiments, circumscribing) the aperture 112. In one embodiment, at least a portion of the rim 114 has a concave configuration that cradles or supports the corneal graft tissue in its normal concave configuration, with the epithelial side of the corneal graft tissue facing the first chamber 92 and the endothelial side of the corneal graft tissue facing the second chamber 94 when the dual-chamber vial 80 is assembled. In one embodiment, the corneal graft tissue support structure 110 is planar, or at least substantially planar, and lies in a plane that is orthogonal to, or at least substantially orthogonal to, the longitudinal axis 82. However, it will be understood that the corneal graft tissue support structure 110 may have another shape, such as convex or concave. When the dual-chamber vial 80 is assembled (or at least when the first and second portions 84, 86 are coupled together), the first portion 84 and the second portion 86 together define the first chamber 92.

Continuing to refer to FIG. 12, in one embodiment, the rim 108 has an outer diameter that is less than the outer diameter of the wall 106 (that is, the rim 108 is closer to the longitudinal axis 82 than the wall 106), and each of the at least one tab 98A protrudes from the wall of the rim 108 by a distance that is between approximately 50% to approximately 150% (±10%) of the distance between the rim 108 and the wall 106. However, it will be understood that the at least one tab 98A may protrude by a distance that is less than or greater than this range. In one embodiment, the at least one tab 98A protrudes from the wall of the rim 108. In one embodiment, the at least one tab 98A includes two tabs 98A that are opposite each other (that is, positioned at 180°, or at least 180°±5° from each other). Further, in one embodiment, the at least one slot 96B is defined by the wall 106 and includes two slots 96B that are opposite each other (that is, positioned at 180°, or at least 180°±5° from each other) and vertically aligned with the tab(s) 98A. In one embodiment, the corneal graft tissue support structure 110 is flat or at least substantially flat, although it will be understood that the corneal graft tissue support structure 110 may have another shape, such as convex or concave. When the dual-chamber vial 80 is assembled (or at least when the first and second portions 84, 86 are coupled together), the first portion 84 and the second portion 86 together define the first chamber 92.

As is best seen in FIG. 12, in one embodiment, the third portion 88 generally includes an annular body portion 120 and a corneal graft tissue retainment structure 122 extending between the inner surface 123 of the annular body portion 120. When the dual-chamber vial 80 is assembled, the corneal graft tissue support structure 110 and the corneal graft tissue retainment structure 122 may together be referred to as the corneal graft tissue suspension assembly. In one embodiment, the annular body portion 120 extends beyond (that is, above when the dual-chamber vial 80 is assembled) the corneal graft tissue retainment structure 122, thereby at least partially defining the second chamber 94. In one embodiment, the corneal graft tissue retainment structure 122 is shaped substantially similar to the corneal graft tissue retainment structure 40 of FIGS. 1-8 and generally includes an annular structure 124 defining a central aperture 126 and an engagement rim 128, and a plurality of radial spokes 130 extending between the annular structure 124 and the inner surface 123 of the annular body portion 120. Thus, the central aperture 126 is within and coaxial with the annular body portion 120. In one embodiment, the annular body portion 120 also includes an annular groove 131 in the upper rim that is sized and configured to receive and retain therein a gasket (not shown) for ensuring or enhancing a fluid-tight seal between the lid 90 and the third portion 88.

Similarly, one or more other portions of the dual-chamber vial 80 may also include a groove and gasket for ensuring or enhancing fluid-tight seals.

Continuing to refer to FIG. 12, in one embodiment, the annular body portion 120 includes at least one release element 132 that at least partially defines the at least one slot 98B. In one embodiment, each release element 132 includes a grip portion 134 that extends away from the outer surface 135 of the annular body portion 120 (that is, extends away from the longitudinal axis 82), and the annular body portion 120 includes a slit 136 on either side of the release element 132 that at least partially separate the release element 132 from the annular body portion 120 and allow the release element to move or flex relative to the annular body portion 120. For example, to uncouple the third portion 88 from the second portion 86, a user may engage the grip portion(s) 134 and lift or move the grip portion(s) 134 away from the annular body portion 120 to disengage the tab(s) 98A of the second portion 86 from the slot(s) 98B of the third portion 88. In one embodiment, the at least one tab 100A includes two tabs 100A that are opposite each other (that is, positioned at 180°, or at least approximately 180° (±5°) from each other). Further, in one embodiment, the at least one slot 98B includes two slots 98B that are opposite each other (that is, positioned at 180°, or at least approximately 180° (±5°) from each other) and positioned at 90° between the tabs 100A. Put another way, in one embodiment a first tab 100A is centered at approximately 0°, a first slot 98B is centered at approximately 90°, a second tab 100B is centered at approximately 180°, and a second slot 09B is centered at approximately 270° relative to the circumference of the annular body portion 120. Further, in one embodiment, the slot(s) 98B of the third portion 88 are vertically aligned with the tab(s) 98A of the second portion 86 when the dual-chamber vial 80 is assembled.

As is best seen in FIG. 12, in one embodiment the lid 90 generally includes a face 138 surface and at least one release element 140. In one embodiment, the at least one release element 140 includes two release elements 140, and each release element 140 defines a slot 100B. In one embodiment, each release element 140 includes two arms 142 that extend downward from the outer surface of the lid 90 and that are coupled to or meet with a grip portion 144 that extends from that extends away from the outer surface 143 of the lid 90 (that is, extends away from the longitudinal axis 82). The outer surface of the 143 lid 90, the arms 142, and the grip portion 144 together define a slot 100B. In one embodiment, the slots 100B are opposite each other (that is, positioned at 180°, or at least approximately 180° (±5°) from each other) and are vertically aligned with the tabs 100A of the third portion 88 when the dual-chamber vial 80 is assembled. In one embodiment, the face 138 includes an indentation 146 that extends from the face 138 and into the dual-chamber vial 80 toward the third portion 88 (for example, downward when the dual-chamber vial 80 is assembled). Further, when the dual-chamber vial 80 is assembled, the second portion 86, the third portion 88, and the lid 90 together define a second chamber 94, with the indentation 146 at least partially defining the roof or upper surface of the second chamber 94 and providing a viewing surface 148 through which the endothelial side of the corneal graft tissue within the dual-chamber vial 80 can be viewed. Optionally, the face 138 also includes one or more indicia 150 (for example, arrows as shown in FIG. 11-14) that indicate to a user where the release element(s) 140 are for removal of the lid 90. For example, the user may manipulate the grip portion 144 of each release element 140 of the lid 90 to remove the lid 90 in a similar manner as described above for uncoupling the second portion 86 and the third portion 88. In one embodiment, neither the first portion 84 nor the second portion 86 includes release elements, to reduce the likelihood of user uncoupling the first and second portions 84, 86 and unintentionally spilling the first preservation medium 64 from the first chamber 92. Conversely, the lid 90 is easily removed for viewing the corneal graft tissue more closely and/or for replacing the second preservation medium 68, and the second and third portions 86, 88 are easily uncoupled from each other to release the corneal graft tissue 60 for use.

Referring again to FIGS. 11-14, and with reference to FIG. 9, the corneal graft tissue suspension assembly generally lies in a plane that is orthogonal to, or at least substantially orthogonal to, the longitudinal axis 82 of the dual-chamber vial 80 (put another way, in one embodiment the corneal graft tissue suspension assembly is configured to support the corneal graft tissue generally in a plane that bisects the dual-chamber vial 80 into a lower chamber 92 and an upper chamber 94). In one embodiment, the corneal graft tissue suspension assembly generally includes a first element, which includes at least the corneal graft tissue support structure 110, and a second element, which includes at least the corneal graft tissue retainment structure 122, and the first and second elements are configured to be vertically and horizontally aligned when the dual-chamber vial 80 is assembled. Further, in one embodiment there is a gap of between approximately 0.25 mm (±0.05 mm) and approximately 0.85 mm (±0.05 mm) between at least a portion of the first element and at least a portion of the second element (for example, between the engagement rims 114 and 128), such that when the dual-chamber vial 80 is assembled and contains a corneal graft tissue, the corneal graft tissue is suspended between, and may be in contact with each of, the corneal graft tissue support structure 110 of the second portion 86 and the corneal graft tissue retainment structure 122 of the third portion 88. In particular, the epithelial side of the corneal graft tissue rests on the corneal graft tissue support structure 110 such that at least a portion of the epithelial side is exposed through the aperture 112 to the first preservation medium 64 within the first chamber 92 and at least a portion of the epithelial side is in contact with the engagement rim 114 surrounding the aperture 112. Further, when the dual-chamber vial 80 is assembled, the engagement rim 128 of the annular structure 124 of the corneal graft tissue retainment structure 122 circumscribes, but is not in contact with, the endothelial side of the cornea, but is in contact with (or closely proximate) the sclera (for example, the endothelial side of the sclera), as shown in FIG. 9. Although reference numbers associated with the first embodiment of the dual-chamber vial 10 are shown in FIG. 9, it will be understood that corresponding portions of the second embodiment of the dual-chamber vial 80 may be positioned in a like manner relative to corneal graft tissue when the dual-chamber vial 80 is assembled.

Referring now to FIGS. 13 and 14, cross-sectional views of the dual-chamber vial 80 are shown. The wall 104 of the first portion 84 has an outer diameter and the wall 106 of the second portion 84 has an inner diameter. In one embodiment, the outer diameter of the wall 104 is slightly less than the inner diameter of the wall 106, such that the second portion 86 is sized and configured to receive and retain therein the first portion 84, and the first portion 84 fits in close tolerance within the second portion 86. In one non-limiting example, the inner diameter of the wall 106 may be up to 0.015 mm larger than (and not the same as or smaller than) the outer diameter of the wall 104. Further, in one embodiment, the first portion 84 is received within the second portion 86 such that the base 102 of the first portion 84 forms the base of the dual-chamber vial 80, but the wall 104 of the first portion 84 is not visible when the dual-chamber vial 80 is assembled. Likewise, the rim 108 of the second portion 86 has an outer diameter and at least a portion of the annular body portion 120 has an inner diameter that is slightly greater than the outer diameter of the rim 108 such that the third portion 88 is sized and configured to receive and retain therein at least the rim of the second portion 86. Finally, the lid 90 has an outer diameter and the annular body portion 120 has an outer diameter that, in one embodiment, is the same or approximately the same as the outer diameter of the lid 90. Thus, when the dual-chamber vial 80 is assembled, the dual-chamber vial 80 may have at least substantially continuous outer diameter from the base 102 to the lid 90.

In an alternative embodiment of the dual-chamber vial 80, the dual-chamber vial 80 includes threading for coupling the first, second, and third components 84, 86, 88 and the lid 90 together instead of or in addition to the tabs 96A, 98A, 100A and slots 96B, 98B, 100B as shown and described herein and in FIGS. 11-14. For example, in one embodiment, the first portion 84 includes a first threading on an outer surface of the wall 104; the second portion 86 includes a second threading on an inner surface of the wall 106 that is matably couplable to the first threading, as well as a third threading on an outer surface of the rim 108; the third portion 88 includes a fourth threading on an inner surface of, or on a surface within (such as within a groove), the annular body portion 120 that is matably couplable to the third threading, as well as a fifth threading on an inner or outer surface of the annular body portion 120; and the lid 90 includes a sixth threading on an inner or outer surface of the lid that is matably couplable to the fifth threading. Thus, the first and second portions 84, 86 may be screwed together, the second and third portions 86, 88 may be screwed together, and the third portion 88 and the lid 90 may be screwed together to assemble the dual-chamber vial 80. Further, the threadings may be used as coupling means in addition to or instead of the tabs and slots.

Figure 15:
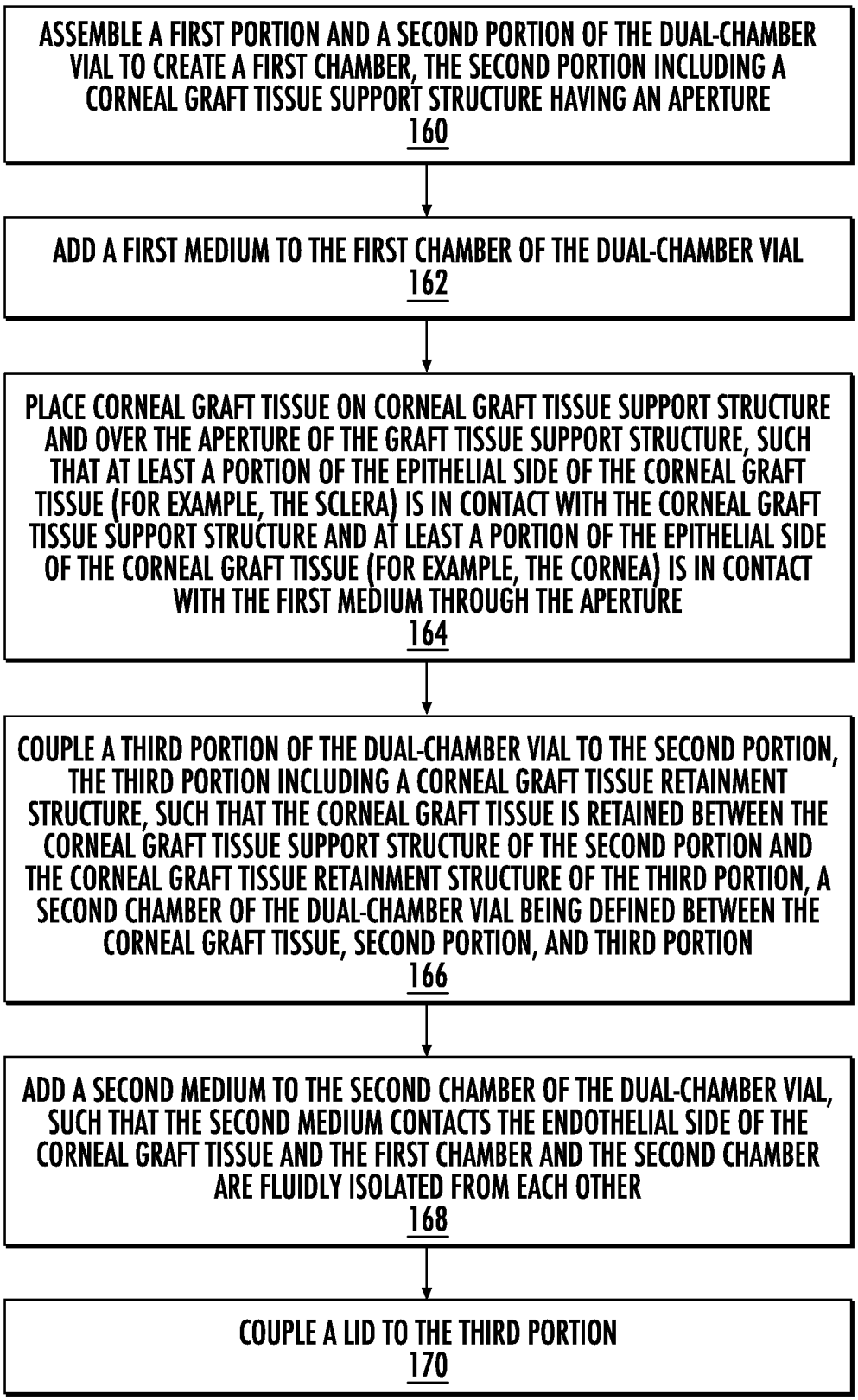
FIG. 15 shows a flow chart of an exemplary method of storing and preserving corneal graft tissue within the dual-chamber vial of FIG. 11, in accordance with the present disclosure.

Referring now to FIG. 15, a flow chart of an exemplary method for storing and preserving corneal graft tissue 60 within the dual-chamber vial 80 is shown. In a first step 160, the first portion 84 and the second portion 86 are coupled together to create the first chamber. As noted above, the second portion 86 includes the corneal graft tissue support structure 110 having an aperture 112. In one embodiment, the tab(s) 96A are aligned with slot(s) 96B and the second portion 86 is pressed downward onto or over the first portion 84 until each tab 96A at least partially extends into its corresponding slot 96B, thereby preventing the first and second portions 84, 86 from being pulled apart. For example, the dual-chamber vial 80 may be sold to a user with the first and second portions 84, 86 already coupled together, but with each of the third portion 88 and the lid 90 being uncoupled from any other component. Alternatively, the dual-chamber vial 80 may be sold to a user in a completely disassembled or uncoupled state. In a second step 162, the first preservation medium 64 (or mixture of media) is added to the first chamber 92, such as through the aperture 112 in the corneal graft tissue support structure 110, until the level of the first preservation medium 64 is level with or immediately proximate the aperture 112.

Continuing to refer to FIG. 15, in a third step 164, corneal graft tissue 60 is placed on the corneal graft tissue support structure 110 such that at least a portion of the epithelium 62

(for example, the sclera 67) is in contact with an upper surface of the engagement rim 114 of the corneal graft tissue support structure 110 and at least a portion of the epithelium 62 (for example, the corneal epithelium 69) is in contact with the first preservation medium 64 through the aperture 112. In a fourth step 166, once the corneal graft tissue 60 is in place, the third portion 88 is coupled to the second portion 86, such as by the method discussed above in the first step 160. For example, the tab(s) 98A are aligned with slot(s) 98B and the third portion 88 is pressed downward onto the second portion 86 until each tab 98A at least partially extends into its corresponding slot 98B, thereby preventing the second and third portions 86, 88 from being pulled apart. Further, when the third portion 88 is coupled to the first portion 86, the engagement rim 128 of the annular structure 124 may be in contact with the endothelial side 66 of the sclera 67, but not the endothelial side 66 of the cornea 69. Thus, the corneal graft tissue 60 is suspended, retained, or otherwise engaged within the dual-chamber vial 80 between the corneal graft tissue support structure 110 and the corneal graft tissue retainment structure 122, and further movement (for example, "sloshing" within the dual-chamber vial 10) of the corneal graft tissue is prevented. Likewise, in some embodiments the corneal graft tissue 60 blocks at least the apertures 112 and 126 to form a fluid-tight seal between the second portion 86 and the third portion 88 and fluidly isolate the first chamber 92 from the second chamber 94.

Continuing to refer to FIG. 15, in a fifth step 168, a second preservation medium 68 (or mixture of media) is added to the second chamber 94, or the portion of the second chamber 94 defined by the third portion 88. In one embodiment, the second preservation medium 68 flows downward through the apertures (central aperture 126 and apertures defined between the radial spokes 130) in the corneal graft tissue retainment structure 122 to come into contact with the endothelium 66 of the corneal graft tissue 60, but is prevented from flowing past the corneal graft tissue 60 and into the first chamber 92 or otherwise contacting the epithelium 62 of the corneal graft tissue 60. In a sixth step 170, the lid 90 is coupled to the third portion 88, such as by the method discussed above in the first step 160. For example, the tab(s) 100A are aligned with slot(s) 100B and the lid 90 is pressed downward onto the third portion 88 until each tab 100A at least partially extends into its corresponding slot 100B, thereby preventing the third portion 88 and the lid 90 from being pulled apart. After this step 170, the dual-chamber vial 80 is fully assembled and fluidly sealed, with the corneal graft tissue 60 safely within. The dual-chamber vial 80 may then be transported and/or stored using any suitable conditions. Further, the epithelial side 62 and/or the endothelial side 66 of the corneal graft tissue 60 may be visualized through the dual-chamber vial 80 (for example, through one or both of the viewing surfaces 103, 148) with the naked eye and/or a viewing device. To remove the corneal graft tissue 60 from the dual-chamber vial 80, the lid 90 is uncoupled from the third portion 88, the second preservation medium 68 removed or poured out, and then the third portion 88 is uncoupled from the second portion 86 and the exposed corneal graft tissue 60 may be removed and used.

Embodiments

In one embodiment, a device (10, 80) for preserving corneal graft tissue comprises: a first chamber (14, 92); a second chamber (18, 94); and a corneal graft tissue suspension assembly (61) that is configured to retain and suspend the corneal graft tissue between the first chamber (14, 92) and the second chamber (18, 94), the first chamber (14, 92) being fluidly isolated from the second chamber (18, 94) when the corneal graft tissue is retained and suspended within the corneal graft tissue suspension assembly.

In one aspect of the embodiment, the corneal graft tissue suspension assembly includes: a first element; and a second element, the first element and the second element being vertically and horizontally aligned with each other when the device (10, 80) is assembled. In one aspect of the embodiment, the device (10, 80) includes a gap between the first element and the second element when the device (10, 80) is assembled. In one aspect of the embodiment, the gap is between approximately 0.25 mm and approximately 0.85 mm.

In one aspect of the embodiment, each of the first element and the second element have a convex configuration.

In one aspect of the embodiment, the device (10) further comprises: a first portion (12), at least a portion of the first portion (12) defining the first chamber (14); and a second portion (16), at least a portion of the second portion (16) defining the second chamber (18), the second portion (16) being removably couplable to the first portion (12). In one aspect of the embodiment, the first portion (12) defines the first element of the corneal graft tissue suspension assembly (61), the first portion (12) and the first element defining the first chamber (14). In one aspect of the embodiment, the first element of the corneal graft tissue suspension assembly (61) includes an aperture (30) located in the center of the first element.

In one aspect of the embodiment, the second portion (16) of the device (10) defines the second element of the corneal graft tissue suspension assembly (61). In one aspect of the embodiment, the second portion (16) of the device (10) includes an annular body portion (34), the second element of the corneal graft suspension assembly (61) having: an annular structure (44) defining a central aperture (46); and a plurality of radial spokes (48) extending between the annular structure (44) and the annular body portion (34), the annular body portion (34) and the second element partially defining the second chamber (18).

In one aspect of the embodiment, the device (10) further comprises a lid (20), the lid (20) being removably couplable to the second portion (16) of the device (10). In one aspect of the embodiment, the annular body portion (34), the second element, and the lid (20) together define the second chamber (18).

In one embodiment, a device (10) for preserving corneal graft tissue (60), the corneal graft tissue (60) having an endothelial side (66) and an epithelial side (62), comprises: a first portion (12), the first portion (12) including: a corneal graft tissue support structure (26) defining an aperture (30); and a first chamber (14) within the first portion (12), the first chamber (14) being at least partially defined by the corneal graft tissue support structure (26); a second portion (16), the second portion (16) including: a corneal graft tissue retainment structure (40); and a second chamber (18) at least partially within the second portion (16), the second chamber (18) being at least partially defined by the corneal graft tissue retainment structure (40); and a lid (20), the second chamber (18) being at least partially defined by the lid (20), the second portion (16) being removably coupled to the first portion (12) and the lid (20) being removably coupled to the second portion (16) when the device (10) is assembled, and the corneal graft tissue support structure (26) and the corneal graft tissue retainment structure (40) being configured to suspend the corneal graft tissue (60) between the first chamber (14) and the second chamber (18) when the device (10) is assembled.

In one aspect of the embodiment, the corneal graft tissue support structure (26) and the corneal graft tissue retainment structure (40) are configured to suspend the corneal graft tissue (60) such that: at least a portion of the epithelial side (62) is in contact with the corneal graft tissue support structure (26); at least a portion of the epithelial side (62) is in contact with a first solution (64) within the first chamber (14); at least a portion of the endothelial side (66) is in contact with the corneal graft tissue retainment structure (40); and at least a portion of the endothelial (66) side is in contact with a second solution (68) within the second chamber (18). In one aspect of the embodiment, the first solution (64) contains dextran and the second solution (68) is a low-dextran or a dextran-free solution.

In one aspect of the embodiment, the first portion (12) includes a first threading (24) on an outer surface; the second portion (16) includes a second threading (36) on an inner surface and a third threading (38) on an outer surface; and the lid (20) includes a fourth threading (54) on an inner surface.

In one aspect of the embodiment, the lid (20) includes an indentation (58) that extends into the second chamber (18).

In one embodiment, a method of preserving corneal graft tissue (60) within a vial (10), the corneal graft tissue (60) having an endothelial side (66) and an epithelial side (62) opposite the endothelial side, comprises: filling a first chamber (14) of the vial (10) with a first medium (64); placing the corneal graft tissue (60) within a corneal graft tissue suspension assembly (61); and filling second chamber (18) of the vial (10) with a second medium (68), the corneal graft tissue suspension assembly (61) being located between the first chamber (14) and the second chamber (18).

In one aspect of the embodiment, the corneal graft tissue suspension assembly (61) includes a corneal graft tissue retainment element (40) and a corneal graft tissue support element (26) with an aperture (30), placing the corneal graft tissue (60) within the corneal graft tissue suspension assembly (61) including: placing the corneal graft tissue (60) on the corneal graft tissue support structure (26) such that at least a portion of the epithelial layer (62) is in contact with the first medium (64) through the aperture (30); and placing the corneal graft tissue retainment structure (40) over the corneal graft tissue (60) and in contact with the endothelial layer (66), the endothelial layer (66) being in contact with the second medium (68) when the second chamber (18) is filled with the second medium (68).

In one aspect of the embodiment, the corneal graft tissue support structure (26) is a component of a first vial portion (12) and the corneal graft tissue retainment structure (40) is a component of a second vial portion (16), placing the corneal graft tissue retainment structure (40) over the corneal graft tissue (60) including coupling the first vial portion (12) and the second vial portion (16) together.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. A device for preserving corneal graft tissue, the device comprising:
    a first chamber;
    a second chamber;
    a first portion;
    a second portion that is removably couplable to the first portion, the first portion and the second portion together defining the first chamber;
    a third portion that is removably couplable to the second portion, the second portion and the third portion partially defining the second chamber; and
    a corneal graft tissue suspension assembly that is configured to retain and suspend the corneal graft tissue between the first chamber and the second chamber such that the first chamber is fluidly isolated from the second chamber, the corneal graft tissue suspension assembly including:
        a first element, the second portion including the first element; and
        a second element, the third portion including an annular body portion and the second element, the second element including an annular structure defining a central aperture and a plurality of radial spokes extending between the annular structure and an inner surface of the annular body portion, the central aperture being coaxial with the annular body portion, and the annular body portion partially defining the second chamber,
        the first element and the second element being vertically and horizontally aligned with each other when the device is assembled, the corneal graft tissue suspension assembly being configured to retain and suspend the corneal graft tissue between at least a portion of the first element and at least a portion of the second element, the device including a gap between the first element and the second element when the device is assembled.

2. The device of claim 1, wherein the gap is between approximately 0.25 mm and approximately 0.85 mm.

3. The device of claim 1, wherein:
    the first element includes a corneal graft tissue support structure defining a first aperture; and
    the second element includes a corneal graft tissue retainment structure defining a second aperture, the first and second apertures being configured to be vertically and horizontally aligned when the device is assembled.

4. The device of claim 1, further comprising:
    a lid that is removably couplable to the third portion, the lid, the third portion, and at least a portion of the second portion together defining the second chamber.

5. The device of claim 4, wherein the device further comprises a longitudinal axis extending from the first portion to the lid, the first element of the corneal graft tissue suspension assembly including an at least substantially planar portion that lies in a plane that is at orthogonal to the longitudinal axis.

6. A device for preserving corneal graft tissue, the device comprising:
    a first chamber;
    a second chamber;
    a corneal graft tissue suspension assembly that is configured to retain and suspend the corneal graft tissue between the first chamber and the second chamber such that the first chamber is fluidly isolated from the second chamber;
    a first portion;
    a second portion that is removably couplable to the first portion, the first portion and the second portion together defining the first chamber, the second portion including a first element of the corneal graft tissue suspension assembly;

a third portion that is removably couplable to the second portion, the third portion including an annular body portion and a second element of the corneal graft tissue suspension assembly, the second element of the corneal graft tissue suspension assembly including:
  an annular structure defining a central aperture; and
  a plurality of radial spokes extending between the annular structure and an inner surface of the annular body portion, the central aperture being coaxial with the annular body portion and the annular body portion partially defining the second chamber;

a lid that is removably couplable to the third portion, the lid, the third portion, and at least a portion of the second portion together defining the second chamber; and a longitudinal axis extending from the first portion to the lid, the second element of the corneal graft tissue suspension assembly lying in a plane that is orthogonal to the longitudinal axis.

7. A device for preserving corneal graft tissue, the device comprising:
  a first chamber;
  a second chamber;
  a corneal graft tissue suspension assembly that is configured to retain and suspend the corneal graft tissue between the first chamber and the second chamber such that the first chamber is fluidly isolated from the second chamber;
  a first portion;
  a second portion that is removably couplable to the first portion, the first portion and the second portion together defining the first chamber;
  a third portion that is removably couplable to the second portion; and
  a lid that is removably couplable to the third portion, the lid, the third portion, and at least a portion of the second portion together defining the second chamber,
  wherein:
    the first portion includes at least one first tab;
    the second portion includes at least one first slot and at least one second tab, the at least one first slot being configured to matingly accept the at least one first tab;
    the third portion includes at least one second slot and at least one third tab, the at least one second slot being configured to matingly and removably accept the at least one second tab; and
    the lid includes at least one third slot, the at least one third slot being configured to matingly and removably accept the at least one third tab.

8. The device of claim 7, wherein:
  the at least one first tab includes two first tabs that are positioned approximately 180° from each other;
  the at least one first slot includes two first slots that are positioned approximately 180° from each other;
  the at least one second tab includes two second tabs that are positioned approximately 180° from each other and are vertically aligned with the two first slots;
  the at least one second slot includes two second slots that are positioned approximately 180° from each other;
  the at least one third tab includes two third tabs that are positioned approximately 180° from each other and are horizontally aligned with the two second slots; and
  the at least one third slot includes two third slots that are positioned approximately 180° from each other.

9. The device of claim 7, wherein the device further comprises a longitudinal axis, each of the at least one second slot and the at least one third slot including a release element, each release element including a grip portion that extends away from the longitudinal axis.

* * * * *